US012632105B2

(12) United States Patent
Fukasawa et al.

(10) Patent No.: US 12,632,105 B2
(45) Date of Patent: May 19, 2026

(54) INFORMATION PROCESSING APPARATUS, INFORMATION PROCESSING METHOD, AND INFORMATION PROCESSING PROGRAM

(71) Applicant: Sony Group Corporation, Tokyo (JP)

(72) Inventors: Naofumi Fukasawa, Tokyo (JP); Yasutaka Fukumoto, Tokyo (JP); Tetsuro Sato, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/838,242

(22) PCT Filed: Feb. 8, 2023

(86) PCT No.: PCT/JP2023/004169
§ 371 (c)(1),
(2) Date: Aug. 14, 2024

(87) PCT Pub. No.: WO2023/176210
PCT Pub. Date: Sep. 21, 2023

(65) Prior Publication Data
US 2025/0147576 A1     May 8, 2025

(30) Foreign Application Priority Data
Mar. 16, 2022    (JP) ................................ 2022-041155

(51) Int. Cl.
*G06F 3/01*          (2006.01)
*A61B 5/00*          (2006.01)
(Continued)

(52) U.S. Cl.
CPC ............ *G06F 3/011* (2013.01); *A61B 5/0077* (2013.01); *A61B 5/1116* (2013.01);
(Continued)

(58) Field of Classification Search
CPC . G06F 3/011; G06T 7/75; G06T 7/251; G06T 11/00; G06T 2207/30196;
(Continued)

(56) References Cited

U.S. PATENT DOCUMENTS

| | | |
|---|---|---|
| 10,139,914 B2 | 11/2018 | Elangovan |
| 2010/0164862 A1 | 7/2010 | Sullivan |

(Continued)

FOREIGN PATENT DOCUMENTS

| | | |
|---|---|---|
| JP | 2003-106812 A | 4/2003 |
| WO | WO 2019/203188 A1 | 10/2019 |

*Primary Examiner* — Robert J Michaud
(74) *Attorney, Agent, or Firm* — Paratus Law Group, PLLC

(57) ABSTRACT

An information processing apparatus (100) according to an embodiment of the present disclosure includes: a first acquisition unit configured to acquire, from an inertial sensor attached to a moving body, inertial information associated with a movement of the moving body; a second acquisition unit configured to acquire first image information obtained by imaging the moving body from a first camera; and a calculation unit configured to calculate third posture information on the basis of first posture information of the moving body obtained on the basis of the inertial information acquired by the first acquisition unit and second posture information of the moving body obtained on the basis of the first image information acquired by the second acquisition unit.

20 Claims, 26 Drawing Sheets

(51) Int. Cl.

| | | |
|---|---|---|
| *A61B 5/11* | (2006.01) | |
| *G06T 7/246* | (2017.01) | |
| *G06T 7/73* | (2017.01) | |
| *G06T 11/00* | (2006.01) | |

(52) U.S. Cl.
CPC ............ *A61B 5/1128* (2013.01); *G06T 7/251* (2017.01); *G06T 7/75* (2017.01); *G06T 11/00* (2013.01); *A61B 2562/0219* (2013.01); *G06T 2207/30196* (2013.01)

(58) Field of Classification Search
CPC ... A61B 5/0077; A61B 5/1116; A61B 5/1128; A61B 2562/0219
See application file for complete search history.

(56) References Cited

U.S. PATENT DOCUMENTS

| | | | | |
|---|---|---|---|---|
| 2015/0339026 | A1* | 11/2015 | Phang | H04N 21/42222 |
| | | | | 348/552 |
| 2016/0049011 | A1* | 2/2016 | Kasahara | G06F 3/04815 |
| | | | | 345/633 |
| 2016/0360970 | A1* | 12/2016 | Tzvieli | A61B 5/0075 |
| 2020/0364447 | A1 | 11/2020 | Nishiyama | |
| 2021/0263333 | A1* | 8/2021 | Amano | A61B 5/6803 |
| 2022/0066544 | A1* | 3/2022 | Kwon | G06V 20/41 |
| 2025/0216931 | A1* | 7/2025 | Butcher | G06T 13/40 |

* cited by examiner

Figure 12:
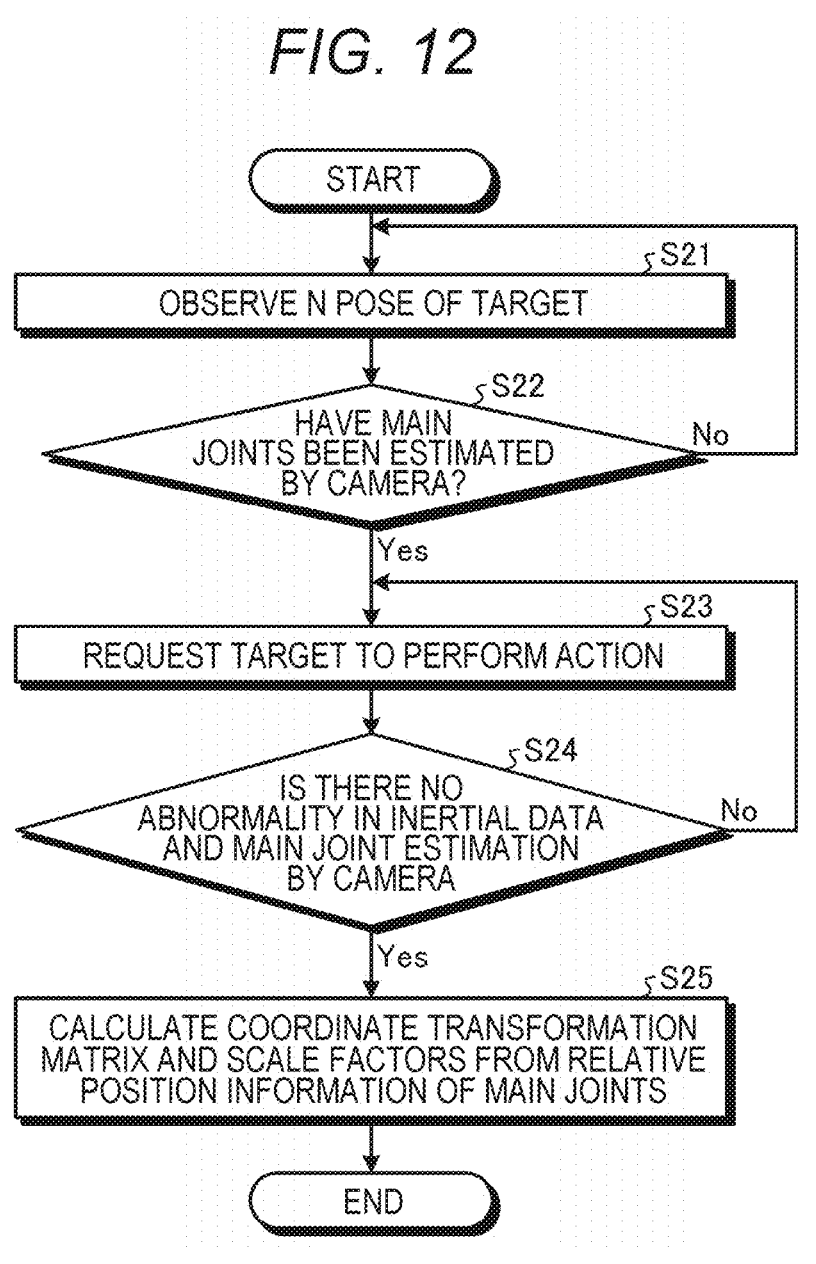

START

OBSERVE N POSE OF TARGET ⌐S21

HAVE MAIN JOINTS BEEN ESTIMATED BY CAMERA? ⌐S22
No

Yes

REQUEST TARGET TO PERFORM ACTION ⌐S23

IS THERE NO ABNORMALITY IN INERTIAL DATA AND MAIN JOINT ESTIMATION BY CAMERA ⌐S24
No

Yes

CALCULATE COORDINATE TRANSFORMATION MATRIX AND SCALE FACTORS FROM RELATIVE POSITION INFORMATION OF MAIN JOINTS ⌐S25

END

*FIG. 21*

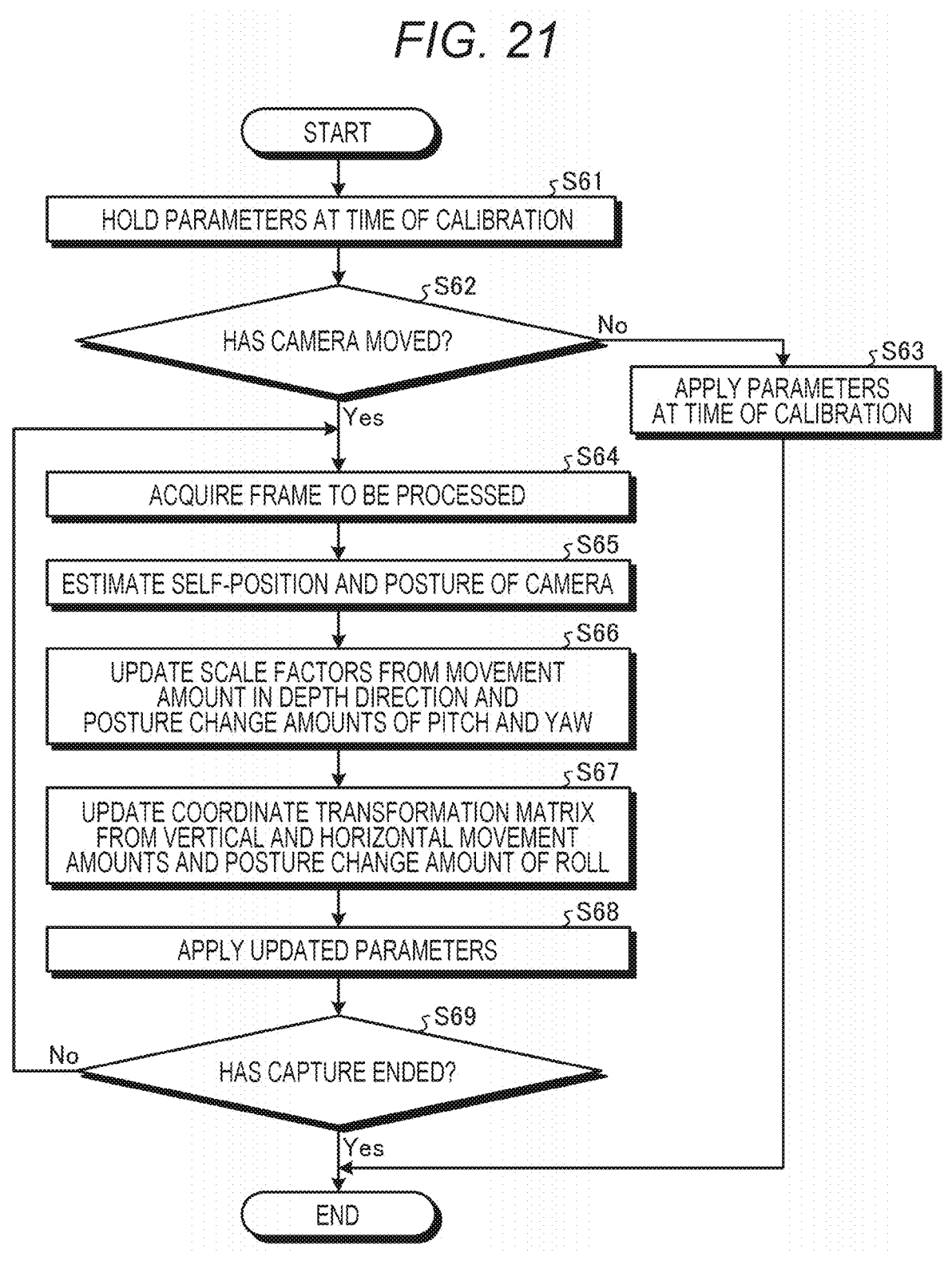

START

S61

HOLD PARAMETERS AT TIME OF CALIBRATION

S62

HAS CAMERA MOVED?    No

S63

APPLY PARAMETERS
AT TIME OF CALIBRATION

Yes

S64

ACQUIRE FRAME TO BE PROCESSED

S65

ESTIMATE SELF-POSITION AND POSTURE OF CAMERA

S66

UPDATE SCALE FACTORS FROM MOVEMENT
AMOUNT IN DEPTH DIRECTION AND
POSTURE CHANGE AMOUNTS OF PITCH AND YAW

S67

UPDATE COORDINATE TRANSFORMATION MATRIX
FROM VERTICAL AND HORIZONTAL MOVEMENT
AMOUNTS AND POSTURE CHANGE AMOUNT OF ROLL

S68

APPLY UPDATED PARAMETERS

S69

No    HAS CAPTURE ENDED?

Yes

END

INFORMATION PROCESSING APPARATUS, INFORMATION PROCESSING METHOD, AND INFORMATION PROCESSING PROGRAM

CROSS REFERENCE TO PRIOR APPLICATION

This application is a National Stage Patent Application of PCT International Patent Application No. PCT/JP2023/004169 (filed on Feb. 8, 2023) under 35 U.S.C. § 371, which claims priority to Japanese Patent Application No. 2022-041155 (filed on Mar. 16, 2022), which are all hereby incorporated by reference in their entirety.

TECHNICAL FIELD

The present disclosure relates to an information processing apparatus, an information processing method, and an information processing program related to motion capture processing.

BACKGROUND ART

In recent years, a motion capture technology for acquiring movement information indicating a movement of a user has been actively developed. The acquired movement information is used for, for example, action instruction in sports and rehabilitation or used for applications such as virtual reality (VR) or augmented reality (AR). Furthermore, an avatar video imitating the movement of the user is generated using the acquired movement information, and also distribution of the avatar video is conducted.

Note that as a method for implementing the motion capture technology, an optical method using a marker, an inertial sensor method using an acceleration sensor, and the like, a camera method for analyzing a video, and the like are known. For example, Patent Document 0 discloses a motion capture technology implemented by an inertial sensor method using inertial navigation system (INS).

CITATION LIST

Patent Document

Patent Document 1: WO 2019/203188 A

SUMMARY OF THE INVENTION

Problems to be Solved by the Invention

However, since the inertial navigation system calculates a position by integrating an acceleration included in inertial sensor data a plurality of times, there is a problem that an error of the obtained position increases with time. The technique described in Patent Document 1 is a technique for obtaining position information by an inertial sensor method with higher accuracy, but it is desirable to have a technique capable of further improving accuracy in combination with or in place of the technique of Patent Document 1.

Therefore, the present disclosure proposes an information processing apparatus, an information processing method, and an information processing program capable of improving the accuracy of motion capture.

Solutions to Problems

To solve the above-described problem, an information processing apparatus according to an embodiment of the present disclosure includes: a first acquisition unit configured to acquire, from an inertial sensor attached to a moving body, inertial information associated with a movement of the moving body; a second acquisition unit configured to acquire first image information obtained by imaging the moving body from a first camera; and a calculation unit configured to calculate third posture information on the basis of first posture information of the moving body obtained on the basis of the inertial information acquired by the first acquisition unit and second posture information of the moving body obtained on the basis of the first image information acquired by the second acquisition unit.

BRIEF DESCRIPTION OF DRAWINGS

FIG. 6 is a diagram (2) illustrating an example of generation of corrected skeleton data.

FIG. 12 is a flowchart illustrating a processing procedure of calibration according to the embodiment.

FIG. 21 is a flowchart illustrating a procedure of information processing according to a fifth modification.

3

Figure 22:
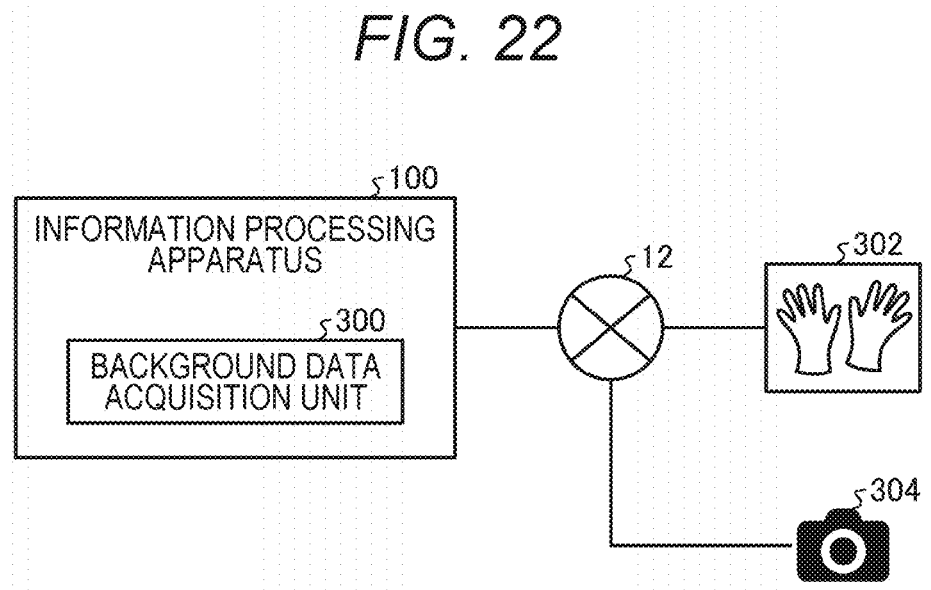

FIG. 22 is a diagram illustrating a configuration example of a system that executes information processing according to a sixth modification.

Figure 23:
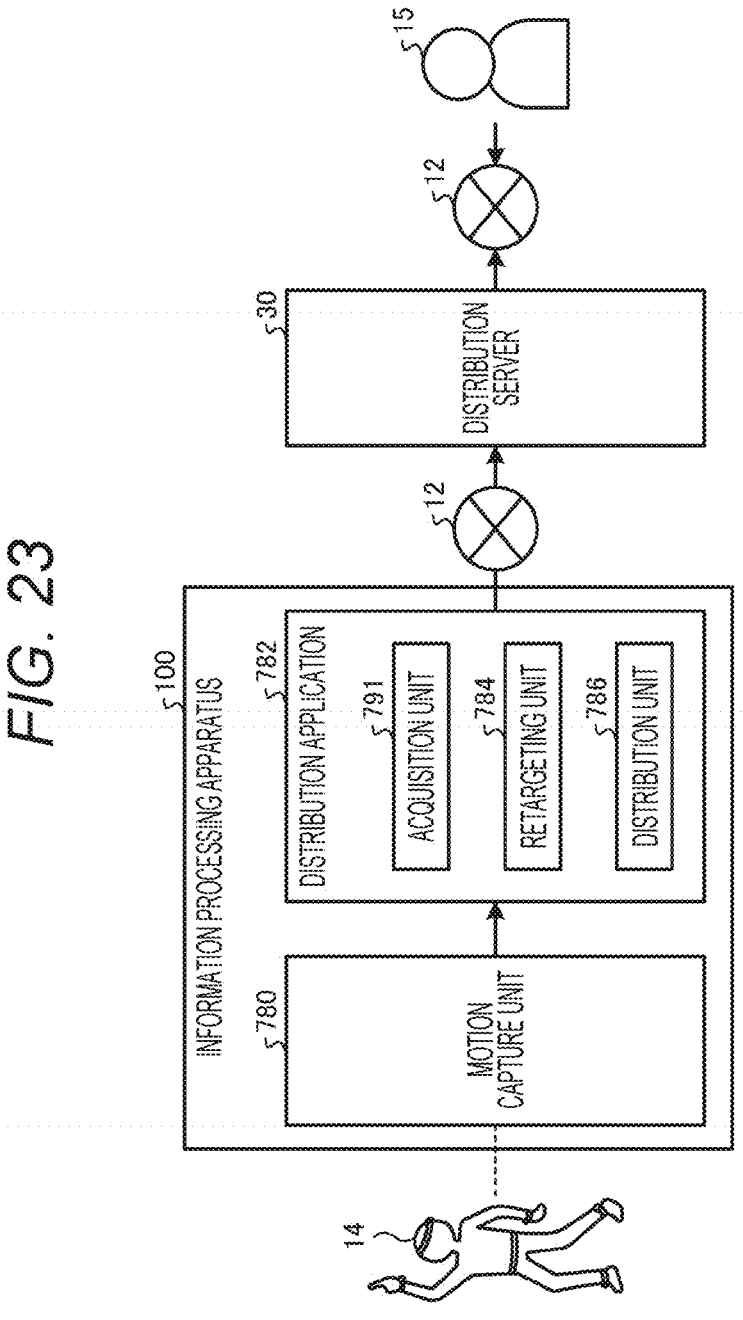

FIG. 23 is a diagram illustrating use case 1 of the seventh modification.

Figure 24:
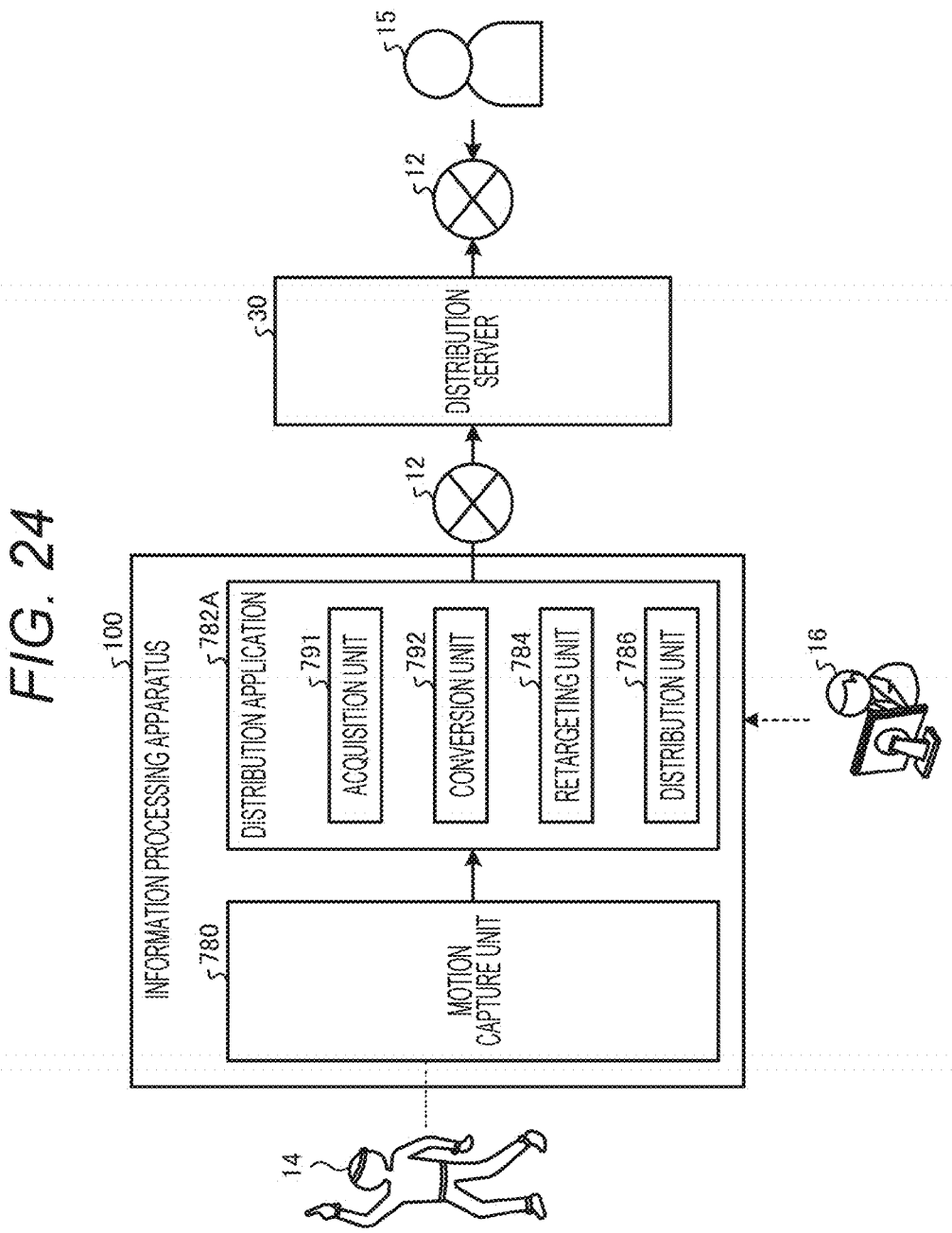

FIG. 24 is a diagram illustrating use case 2 of the seventh modification.

Figure 25:
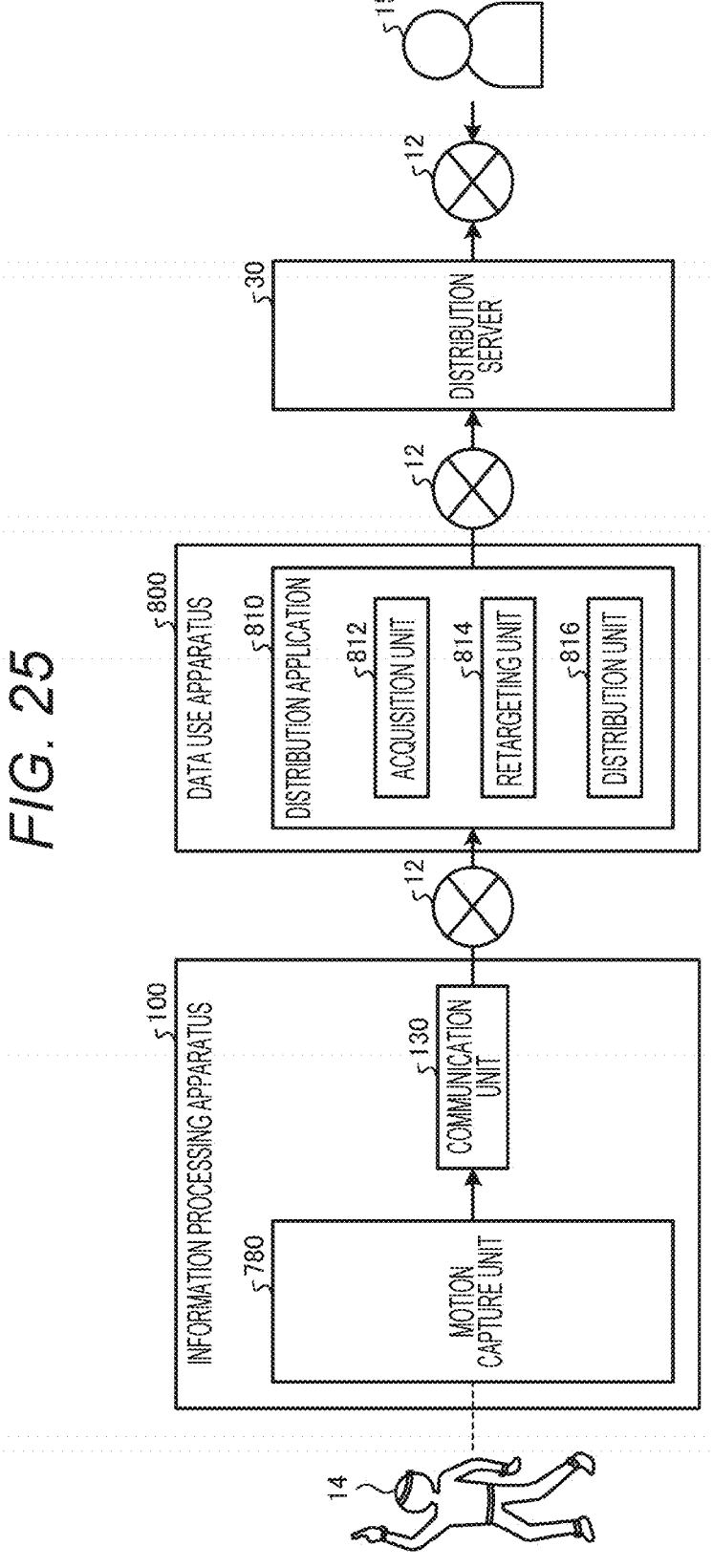

FIG. 25 is a diagram illustrating use case 3 of the seventh modification.

Figure 26:
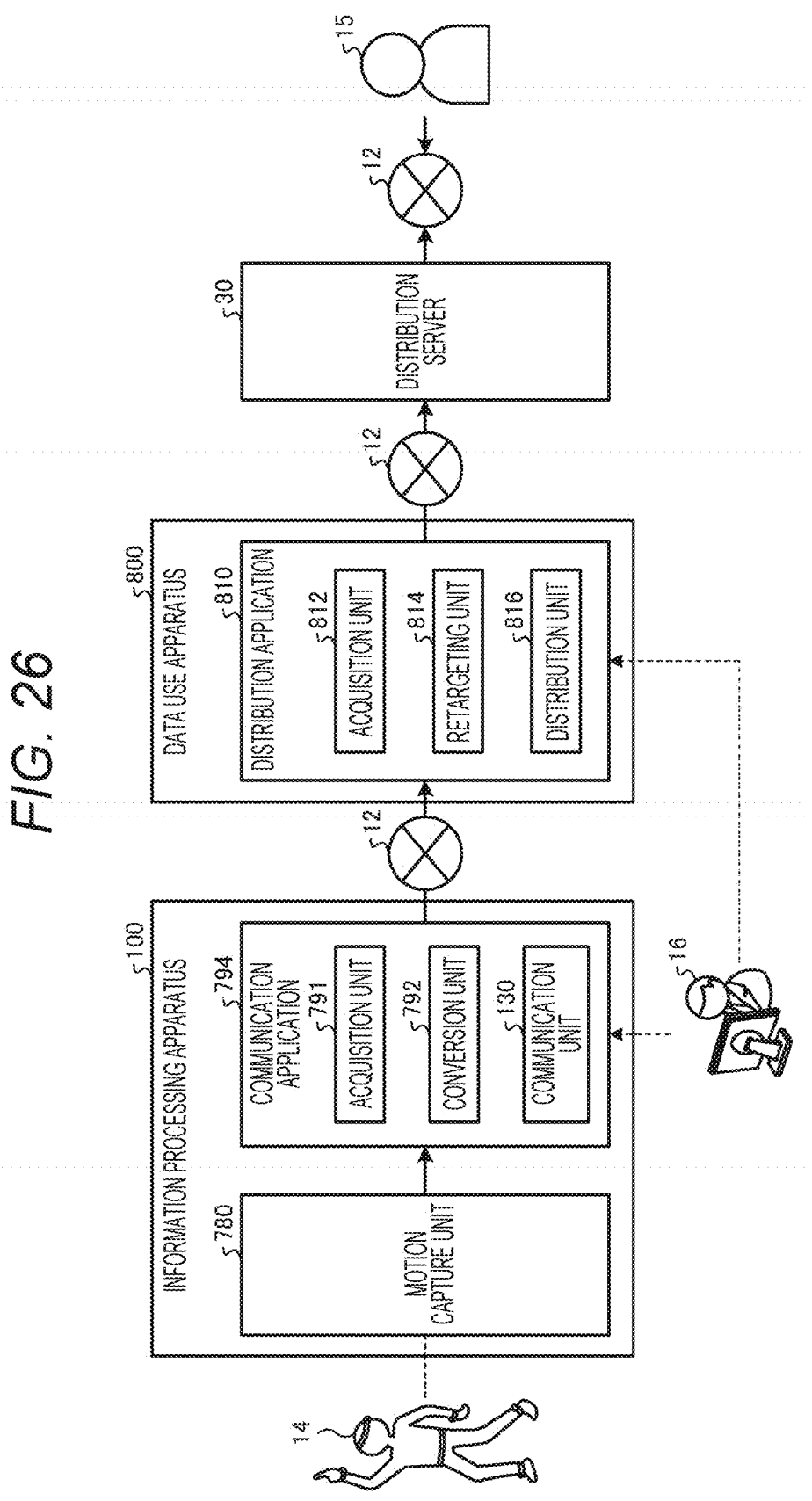

FIG. 26 is a diagram illustrating use case 4 of the seventh modification.

Figure 27:
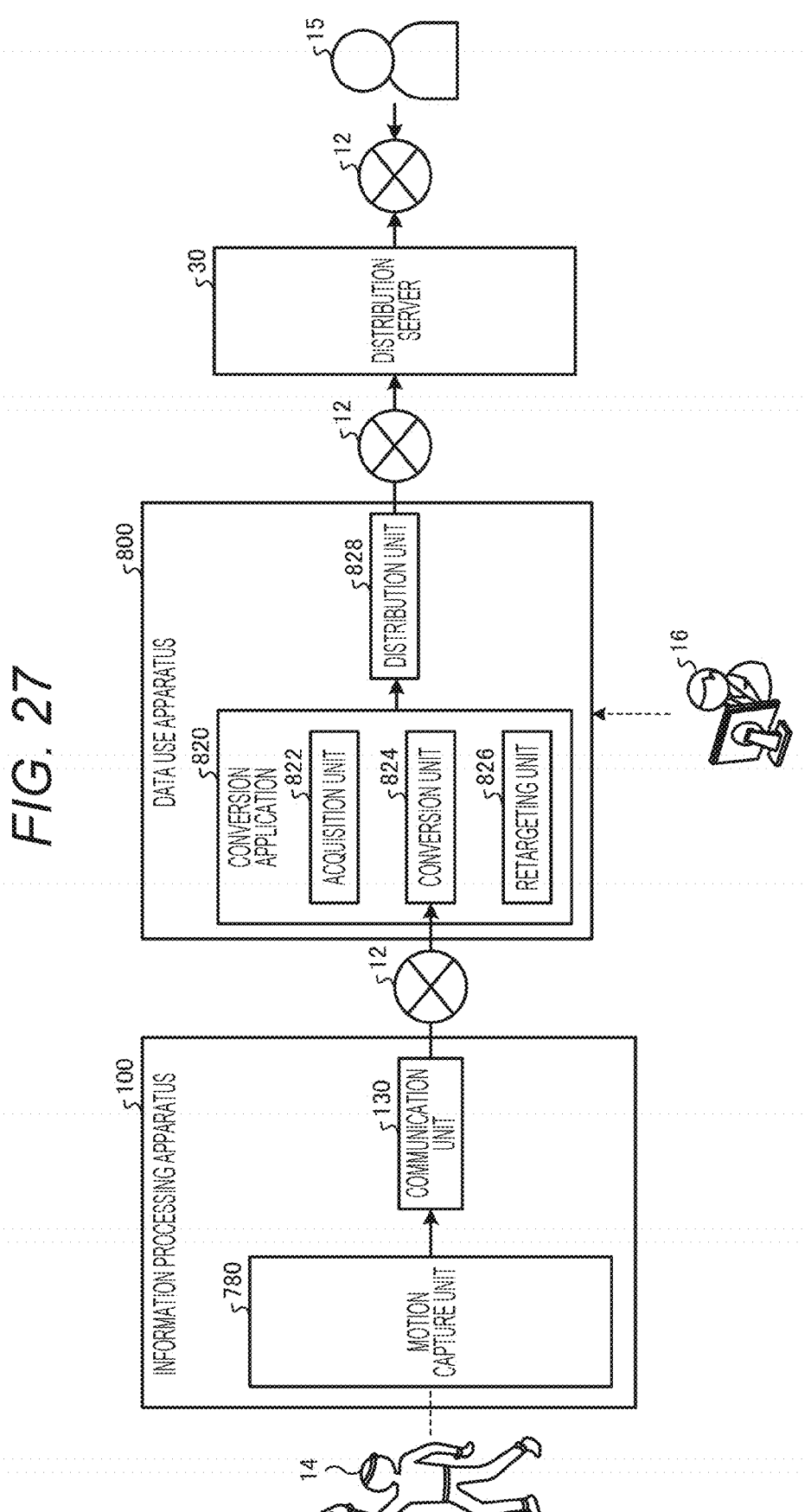

FIG. 27 is a diagram illustrating use case 5 of the seventh modification.

Figure 28:
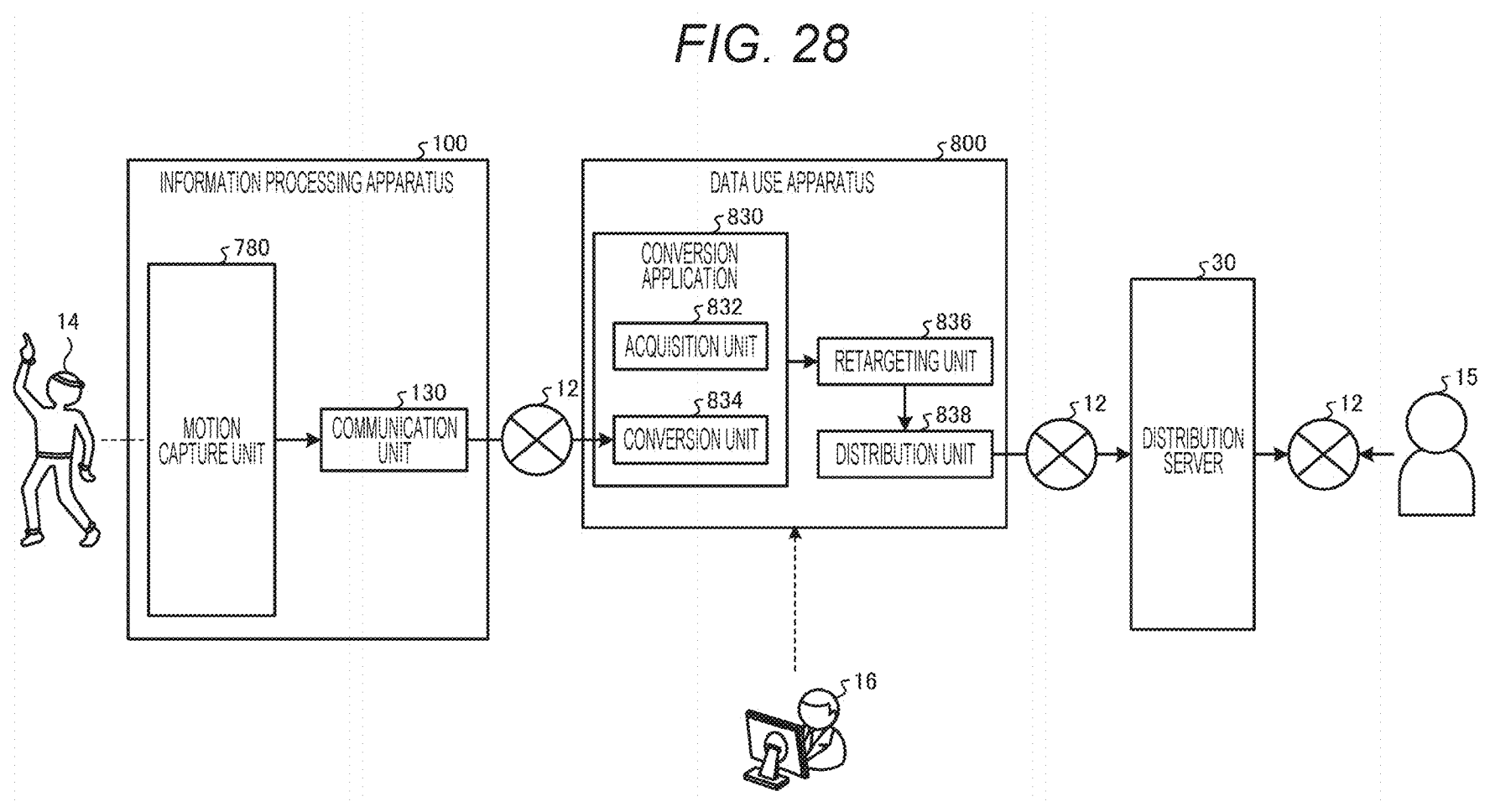

FIG. 28 is a diagram illustrating use case 6 of the seventh modification.

Figure 29:
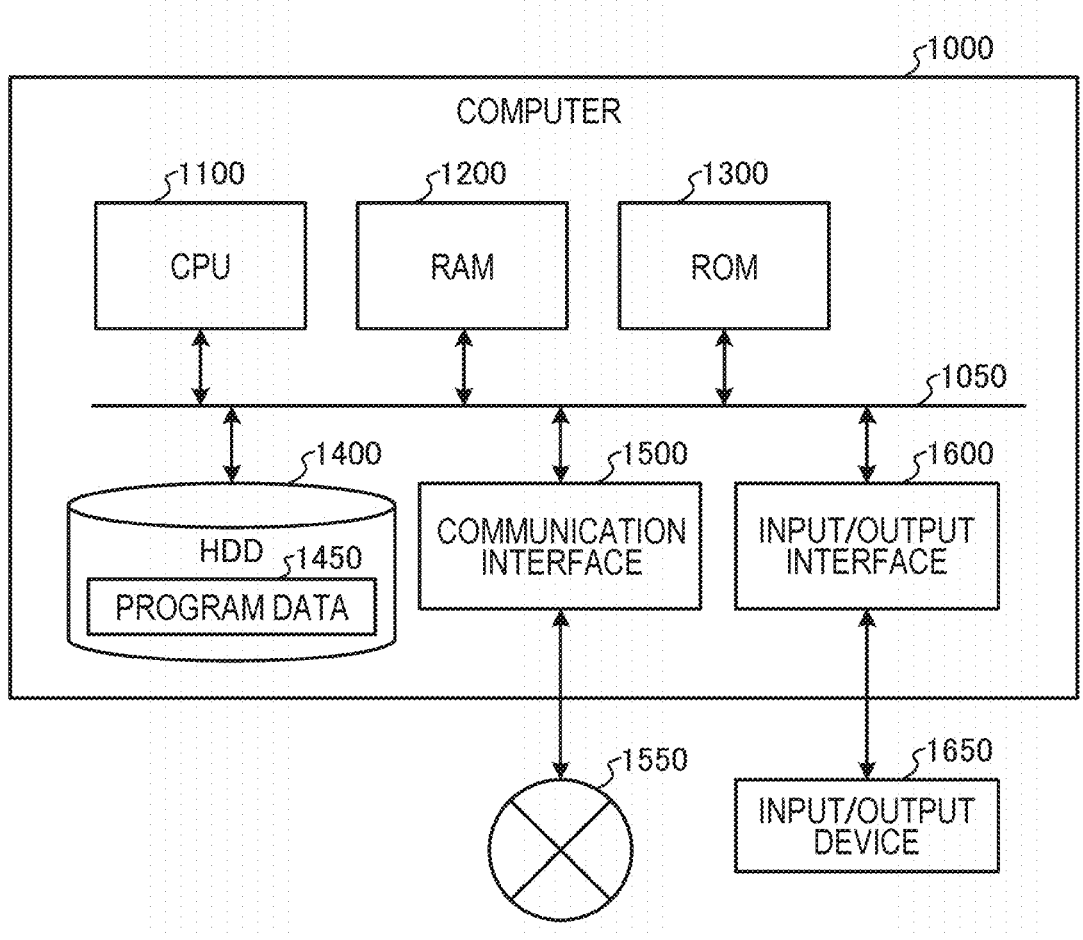

FIG. 29 is a hardware configuration diagram illustrating an example of a computer that implements a function of the information processing apparatus.

MODE FOR CARRYING OUT THE INVENTION

Hereinafter, embodiments will be described in detail on the basis of the drawings. Note that in each of the following embodiments, the same parts are denoted by the same reference numerals, and redundant description will be omitted.

The present disclosure will be described according to the following order of items.

Figure 1:
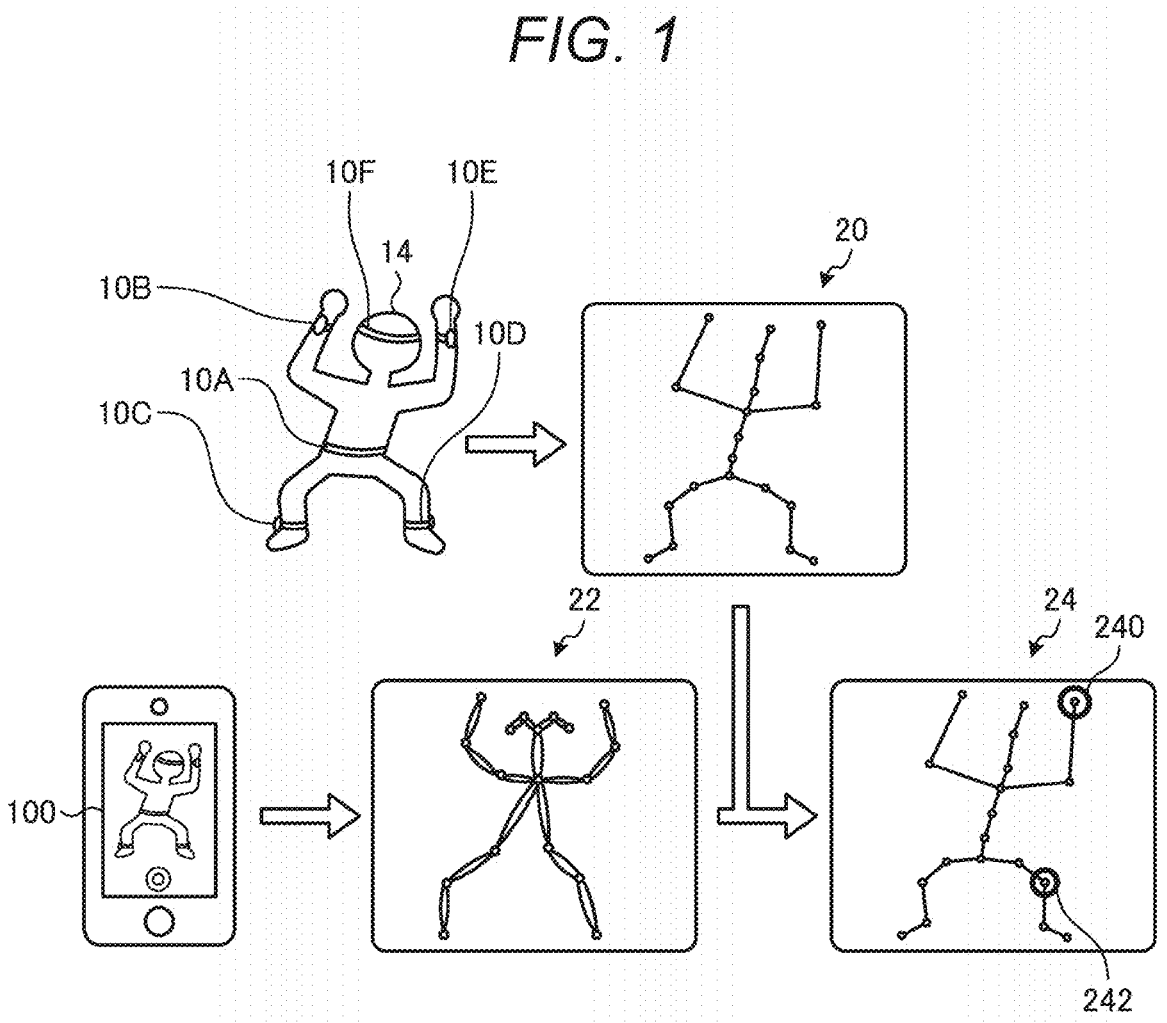
FIG. 1 is a diagram illustrating an outline of information processing according to an embodiment.

1. Embodiment
1-1. Outline of Information Processing According to Embodiment
1-2. Configuration of Information Processing System According to Embodiment
1-3. Configuration of Information Processing Apparatus According to Embodiment
1-4. Processing Procedure of Information Processing System According to Embodiment
1-5. Modification of Embodiment
1-5-1. Real-time Processing
1-5-2. Post-Process Processing
1-5-3. Use Example of Additional Information Obtained from Camera
1-5-4. Capture Example of Plurality of Moving Bodies
1-5-5. Use of Self-position Estimation of Camera
1-5-6. System Configuration Example in Case of Using External Device
1-5-7. Modification of Information Processing System
2. Other Embodiments
3. Effects of Information Processing Apparatus According to Present Disclosure
4. Hardware Configuration 1. Embodiment 1-1. Outline of Information Processing According to Embodiment FIG. 1 is a diagram illustrating an outline of information processing according to an embodiment. Information processing for visualization of motion of a moving body according to the embodiment is executed by an information processing apparatus 100 illustrated in FIG. 1. For example, the information processing apparatus 100 according to the embodiment measures a movement (motion) of a moving body such as a human, and executes information processing related to so-called motion capture that visualizes the motion on the basis of measured data.

For the visualization of movement information of the moving body such as a human or an animal, for example, skeleton data expressed by a skeleton structure indicating a body structure is used. The skeleton data includes information of parts and bones that are line segments connecting the parts. Note that a part in the skeleton structure corresponds to, for example, an end part, a joint part, or the like of the body. Furthermore, the bones in the skeleton structure may correspond to, for example, human bones, but the positions and the number of the bones do not necessarily need to match an actual human skeleton.

The positions of the parts in the skeleton data can be acquired by various motion capture technologies. For example, there are a camera-type technique of attaching a marker to each body part and acquiring the position of the marker using an external camera or the like, and a sensor-type technique of attaching a motion sensor to a body part and acquiring position information of the motion sensor on the basis of sensor data acquired by the motion sensor.

Furthermore, the skeleton data has various uses. For example, time-series data of the skeleton data is used for form improvement in sports or used for applications such as VR and AR. Furthermore, an avatar video imitating a movement of a user is generated using the time-series data of the skeleton data, and also the avatar video is distributed.

Hereinafter, as an embodiment of the present disclosure, a configuration example of an information processing system that generates skeleton data using a motion sensor and distributes an avatar video on the basis of the skeleton data will be described. Note that the embodiment of the present disclosure is also applicable to other motion capture technologies and other applications. Furthermore, although a human will be mainly described below as an example of the moving body, the embodiment of the present disclosure can be similarly applicable to other moving bodies such as an animal and a robot. Furthermore, hereinafter, data obtained by various motion capture techniques, such as skeleton data obtained with the movement of the moving body or capture of the movement, and data of an appearance of the moving body obtained by imaging with a camera, may be collectively referred to as "posture information".

In the example illustrated in FIG. 1, the information processing apparatus 100 executes information processing using six sensor devices 10A to 10F attached to respective joints of a user 14. The information processing apparatus 100 is implemented by, for example, a tablet terminal, a smartphone, or the like. Note that the sensor devices 10A to 10F are inertial sensors that acquire sensor data corresponding to the movement of the respective joints or the like of the user 14.

The information processing apparatus 100 receives the sensor data of the sensor devices 10A to 10F, and generates inertial skeleton data 20 of the user 14 using the received sensor data. Furthermore, the information processing apparatus 100 images the appearance of the user 14 using a camera included in the information processing apparatus 100 or an external camera and generates optical skeleton data 22 of the user 14 in parallel with acquisition of the inertial skeleton data 20.

Next, the information processing apparatus 100 generates corrected skeleton data 24 by combining the inertial skeleton data 20 and the optical skeleton data 22. Specifically, the information processing apparatus 100 generates the corrected skeleton data 24 by performing correction processing based on information of the optical skeleton data 22 for the inertial skeleton data 20. That is, the information processing apparatus 100 does not use the inertial skeleton data 20 or the optical skeleton data 22 alone, but corrects information mutually on the basis of the acquired two types of posture information to generate the corrected skeleton data 24. Therefore, the information processing apparatus 100 can acquire the corrected skeleton data 24 that is highly accurate motion capture data as compared with a case of using the inertial skeleton data 20 or the optical skeleton data 22 alone.

Although skeleton structures of the inertial skeleton data 20 and the optical skeleton data 22 may be different from each other, the information processing apparatus 100 performs correction for the joints of common portions of the structures in the present invention. For example, the information processing apparatus 100 sets end joints (arms, ankles, head) and intermediate joints (elbows, shoulders, and knees) as main correction targets. Meanwhile, portions not generally included in the optical skeleton data 22, such as fine joints of a spine in the vicinity of a trunk, are excluded from the targets. Here, unlike an actual end joint (for example, a finger) of a human body, the end joint refers to a joint corresponding to an end as an output value of the skeleton data. A palm or a top of a foot may be set as the end joint, depending on a type of the inertial sensor or the camera to be used. In FIG. 1, an end joint 240 and an end joint 242 in the corrected skeleton data 24 are set as the correction targets.

While the inertial motion capture using the sensor devices 10A to 10F has an advantage that it can be used anywhere regardless of an environment, it is necessary to improve the accuracy of absolute positions and to reduce accumulation of errors that may occur during long-term use. Furthermore, in the optical motion capture, the joints are out of an imaging range depending on a posture of the user 14, and it is difficult to continue to accurately capture the movement of the user 14. Therefore, the information processing apparatus 100 improves the accuracy of motion capture by correcting the inertial skeleton data 20 obtained by the inertial motion capture with the optical skeleton data 22 obtained by camera imaging. For example, data by the inertial motion capture has a disadvantage of an increase in an error with time. However, according to the information processing apparatus 100, such an error is corrected on the basis of data by the camera, it is possible to continue execution of motion capture while maintaining high accuracy for a long time.

1-2. Configuration of Information Processing System According to Embodiment

Figure 2:
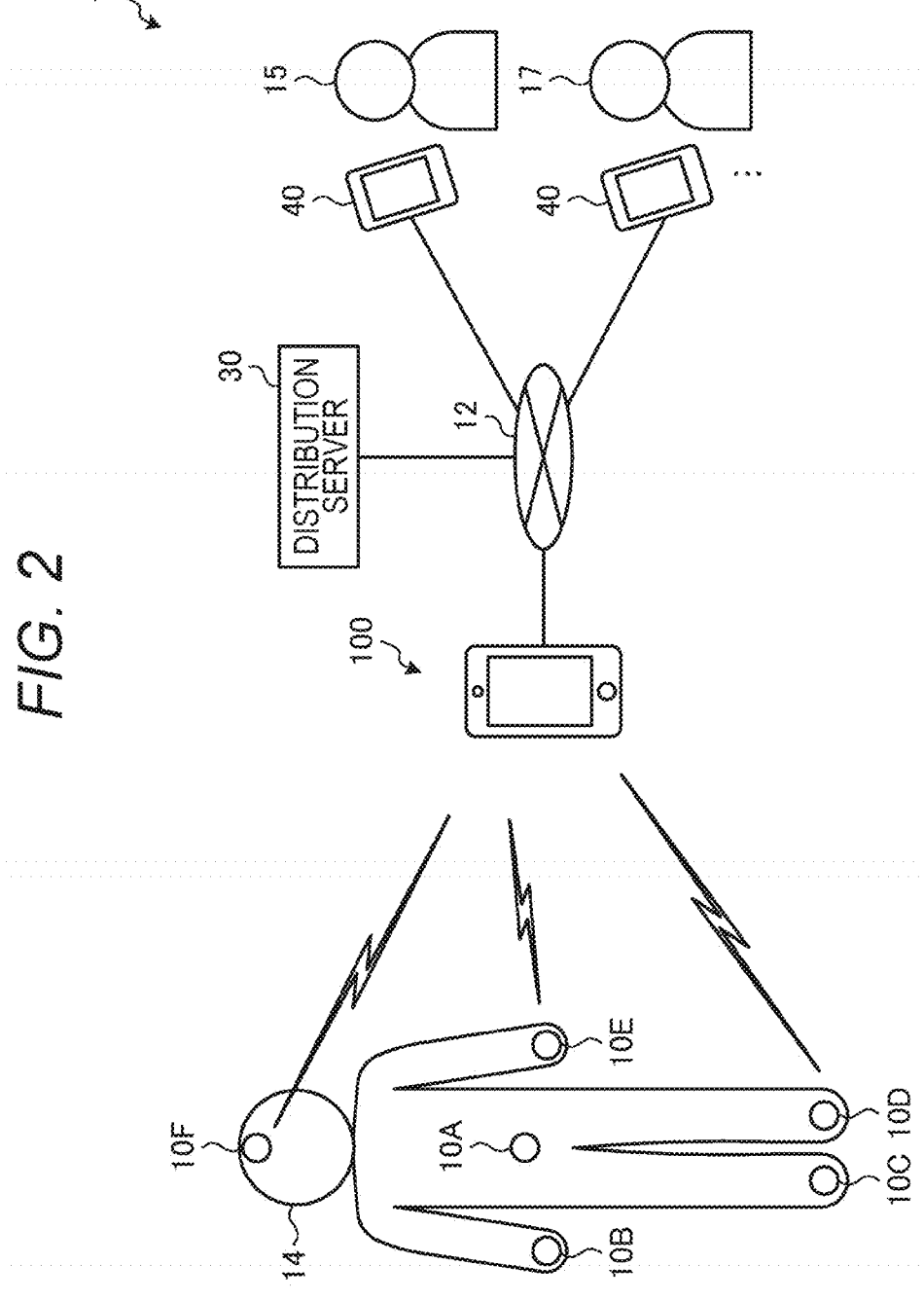
FIG. 2 is a diagram illustrating a configuration of an information processing system according to the embodiment.

FIG. 2 is a diagram illustrating a configuration of an information processing system 1 according to the embodiment. As illustrated in FIG. 2, the information processing system 1 includes the six sensor devices 10A to 10F, the information processing apparatus 100, a distribution server 30, and a viewing user terminal 40.

The information processing apparatus 100, the distribution server 30, and the viewing user terminal 40 are connected via a network 12. The network 12 is a wired or wireless transmission path of information transmitted from a device connected to the network 12. For example, the network 12 may include a public network such as the Internet, a telephone network, or a satellite communication network, various local area networks (LANs) including Ethernet (registered trademark), a wide area network (WAN), and the like. Furthermore, the network 12 may include a dedicated line network such as Internet Protocol-Virtual Private Network (IP-VPN).

The user 14 illustrated in FIG. 2 is a user who distributes an avatar video using the information processing apparatus 100. Users 15 and 17 are viewing users who view the avatar video.

(Sensor Device 10)

The sensor devices 10A to 10F include, for example, an inertial sensor (inertial measurement unit (IMU)) such as an acceleration sensor that acquires acceleration or a gyro sensor (angular velocity sensor) that acquires angular velocity. Note that the sensor devices 10A to 10F may include a sensor such as a geomagnetism sensor, an ultrasonic sensor, or an atmospheric pressure sensor. Furthermore, hereinafter, in a case where it is not necessary to distinguish the sensor devices 10A to 10F, the sensor devices are collectively referred to as sensor device(s) 10.

It is desirable that the sensor device 10 is attached to a joint part (for example, the waist or the head) that serves as a reference of the body or to a vicinity of an end of the body (a wrist, an ankle, the head, or the like). In the example illustrated in FIG. 2, the sensor device 10A is attached to the waist of the user 14, the sensor devices 10B and 10E are attached to the wrists, the sensor devices 10C and 10D are attached to the ankles, and the sensor device 10F is attached to the head. Note that, hereinafter, there may be a case where the body part to which the sensor device 10 is attached may also be referred to as an attached part. Furthermore, the number and attached positions (positions of the attached parts) of the sensor devices 10 are not limited to the example illustrated in FIG. 2, and the number of sensor devices 10 attached to the user 14 may be larger or smaller than the illustrated example.

Such a sensor device 10 acquires acceleration, angular velocity, or the like of the attached part as sensor data, and transmits the sensor data to the information processing apparatus 100.

(Information Processing Apparatus 100)

The information processing apparatus 100 is an example of an information processing apparatus used by the user 14. The information processing apparatus 100 generates the corrected skeleton data 24 on the basis of the inertial skeleton data 20 generated on the basis of inertial sensor data and the optical skeleton data 22 generated on the basis of captured image data by the camera.

Although details will be described below, the information processing apparatus 100 acquires attached part information indicating a position and a posture of each attached part on the basis of the sensor data, and generates the inertial skeleton data 20 including position information and posture information of each part in the skeleton structure on the basis of the attached part information.

Furthermore, the information processing apparatus 100 includes, for example, one or a plurality of cameras such as an RGB camera and a distance measurement sensor (ToF) inside or outside, and acquires image information that captures the posture of the user 14 by imaging. The information processing apparatus 100 generates the optical skeleton data 22 of the user 14 from the obtained image information. Note that, in the present specification, the image information may include not only pixel data constituting an image but also metadata such as date and time when the image was acquired and camera parameters.

The information processing apparatus 100 generates the corrected skeleton data 24 by combining the inertial skeleton data 20 and the optical skeleton data 22.

Here, the skeleton data is an example of the posture information indicating the movement (that is, the posture at predetermined time intervals) of the user 14. In the present disclosure, the skeleton data at a predetermined one time point may be referred to as a pose. Furthermore, time-series data of poses at consecutive n time points may be referred to as a motion.

Moreover, the information processing apparatus 100 may apply the corrected skeleton data 24 to a virtual object (avatar) used for distribution, and generate the avatar video accompanied by a movement corresponding to the corrected skeleton data 24. The information processing apparatus 100 transmits the generated avatar video to the distribution server 30, and requests the distribution server 30 to distribute the avatar video.

Note that although FIG. 2 illustrates a smartphone as the information processing apparatus 100, the information processing apparatus 100 may be an information processing apparatus such as a notebook personal computer (PC), a desktop PC, or a server. Furthermore, the information processing apparatus 100 may have a mode to perform some functions by a smartphone and perform other functions by an information processing apparatus such as a notebook PC connected via a network.

(Distribution Server 30)

The distribution server 30 distributes the avatar video to the viewing user terminal 40 on the basis of a request from the information processing apparatus 100. The distribution server 30 may be provided by the same business operator as the information processing apparatus 100, or may be provided by another business operator. In a case where another business operator different from the business operator that provides the information processing apparatus 100 operates the distribution server 30, the information processing apparatus 100 requests the distribution server 30 that provides a distribution service specified by the user 14 to distribute the avatar video held by the information processing apparatus 100 itself. That is, although only one distribution server 30 is illustrated in FIG. 2, the distribution servers 30 may exist as many as the number of business operators that provide the distribution service.

(Viewing User Terminal 40)

The viewing user terminal 40 is an information processing apparatus used by the viewing user (for example, the user 15 and the user 17 illustrated in FIG. 2). The viewing user terminal 40 includes a display unit that displays various screens, an operation unit that detects an operation of the viewing user, and a control unit that controls the overall operation of the viewing user terminal 40. For example, the viewing user terminal 40 requests the distribution server 30 to distribute the avatar video of the user 14 on the basis of the operation of the viewing user, and displays the avatar video distributed from the distribution server 30. Although a smartphone is illustrated as the viewing user terminal 40 in FIG. 2, the viewing user terminal 40 may be another information processing apparatus such as a notebook PC and a desktop PC.

Figure 3:
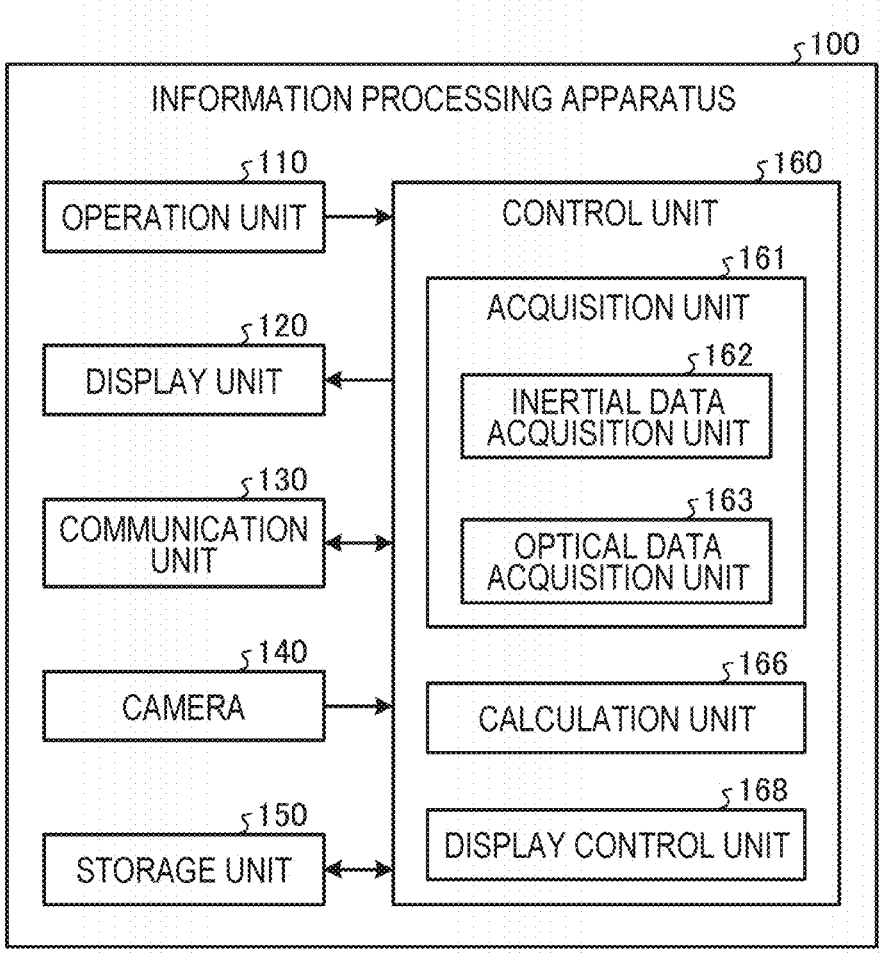
FIG. 3 is a diagram illustrating a configuration of an information processing apparatus according to the embodiment.

1-3. Configuration of Information Processing Apparatus According to Embodiment Next, a configuration of the information processing apparatus 100 according to the embodiment will be described with reference to FIG. 3. FIG. 3 is a diagram illustrating a configuration example of the information processing apparatus 100 according to the embodiment. As illustrated in FIG. 3, the information processing apparatus 100 according to the first embodiment of the present disclosure includes an operation unit 110, a display unit 120, a communication unit 130, a camera 140, a storage unit 150, and a control unit 160.

The operation unit 110 is configured to be operated by the user to input an instruction or information to the information processing apparatus 100.

The display unit 120 displays various display screens. For example, the display unit 120 displays a display screen including the avatar video generated by the control unit 160.

The communication unit 130 transmits the avatar video generated by the control unit 160 to the distribution server 30 via the network 12.

The camera 140 images the user 14 and transmits captured image data to the control unit 160. The camera 140 includes an RGB camera and a distance measurement sensor (ToF). Furthermore, the camera 140 may be one or a plurality of cameras. Furthermore, the camera 140 may be mounted inside the information processing apparatus 100, or may be provided outside and transmit the image information to the control unit 160 via the communication unit 130.

The storage unit 150 stores data to be used for the information processing of the information processing apparatus 100. For example, the storage unit 150 stores avatar information including the image information including body parts such as the head of the avatar, clothes, and accessories. The avatar information may include related information indicating relevance of the image information of each part of the avatar, or may include only one part.

The control unit 160 is implemented by, for example, a central processing unit (CPU), a micro processing unit (MPU), or the like executing a program (for example, an information processing program according to the present disclosure) stored inside the information processing apparatus 100 using a random access memory (RAM) or the like as a work area. Furthermore, the control unit 160 is a controller, and may be implemented by, for example, an integrated circuit such as an application specific integrated circuit (ASIC), or a field programmable gate array (FPGA).

The control unit 160 controls the entire operation of the information processing apparatus 100. The control unit 160 according to the first embodiment of the present disclosure generates the inertial skeleton data 20 of the user 14 on the basis of the sensor data received from the sensor device 10. Furthermore, the control unit 160 generates the optical skeleton data 22 using the image information acquired from the camera 140. Moreover, the control unit 160 corrects the inertial skeleton data 20 on the basis of the optical skeleton data 22 to generate the corrected skeleton data 24. Then, the control unit 160 generates the avatar video having the posture indicated by the corrected skeleton data 24. These functions of the control unit 160 are implemented by an acquisition unit 161, a calculation unit 166, and a display control unit 168 illustrated in FIG. 3.

The acquisition unit 161 includes an inertial data acquisition unit 162 that acquires inertial data received from the sensor device 10, and an optical data acquisition unit 163 that acquires the image information from the camera 140.

The inertial data acquisition unit 162 acquires inertial information associated with the movement of the moving body from an inertial sensor (sensor device 10) attached to the moving body. Specifically, the inertial data acquisition unit 162 acquires the sensor data indicating acceleration, angular velocity, or the like of the attached part from the sensor device 10.

The optical data acquisition unit 163 acquires the image information obtained by imaging the moving body from the camera 140. Specifically, the optical data acquisition unit 163 controls the camera 140 to acquire the image information obtained by imaging the moving body (such as the user 14) to be imaged.

The calculation unit 166 calculates third posture information on the basis of first posture information of the moving body obtained on the basis of the inertial information acquired by the inertial data acquisition unit 162 and second posture information of the moving body obtained on the basis of the image information acquired by the optical data acquisition unit 163. Specifically, the calculation unit 166 calculates the corrected skeleton data 24, which is the third posture information, on the basis of the inertial skeleton data 20 of the user 14 generated on the basis of the inertial information and the optical skeleton data 22 generated on the basis of the image information. That is, the calculation unit 166 calculates the posture information corresponding to the corrected skeleton data 24 from the inertial skeleton data 20 and the optical skeleton data 22, and generates the corrected skeleton data 24 indicating the movement of the moving body.

The calculation processing will be described in detail. Note that, prior to the calculation by the calculation unit 166, the information processing apparatus 100 executes preprocessing (calibration) for associating coordinate systems of the inertial information and the optical information. That is, the calculation unit 166 performs calibration for calculating predetermined parameters such that size and joint information of the user 14 obtained from the inertial data matches size and joint information of the user 14 obtained from the image information, and calculates the corrected skeleton data 24 on the basis of the calibration result. Details of such calibration will be described below.

First, the calculation unit 166 acquires the attached part information indicating the position and posture of each attached part from the inertial data acquisition unit 162, calculates the position information and the posture information of each part in the skeleton structure on the basis of the attached part information, and generates the inertial skeleton data 20 reflecting a calculation result.

Furthermore, the calculation unit 166 calculates the position information and the posture information of the joints of the person and bones between the joints in the image using a skeleton estimation technology on the basis of the image information acquired by the optical data acquisition unit 163, and generates the optical skeleton data 22 reflecting the calculation result.

Thereafter, the calculation unit 166 calculates the posture information related to the corrected skeleton data 24 on the basis of the inertial skeleton data 20 and the optical skeleton data 22. For example, the calculation unit 166 generates the corrected skeleton data 24 by performing correction processing for the inertial skeleton data 20 serving as the basis on the basis of the information of the optical skeleton data 22.

The display control unit 168 performs display control of an object coupled to the movement of the moving body on the basis of the posture information calculated by the calculation unit 166. Specifically, the display control unit 168 performs display control of the avatar on the basis of the corrected skeleton data 24 calculated by the calculation unit 166 and the avatar information stored in the storage unit 150. Specifically, the display control unit 168 generates the image information (including a moving image) of the avatar by applying the corrected skeleton data 24 to the avatar information, and displays the generated avatar. Note that, like such processing, processing of applying the posture information to the virtual object such as the avatar to give a movement may be referred to as "retargeting".

Note that the display control unit 168 may use a background in the image information at the time of generating the optical skeleton data as a background in an avatar image. That is, the display control unit 168 may display the avatar by superimposing the avatar on the image information acquired by the camera 140.

Figure 4:
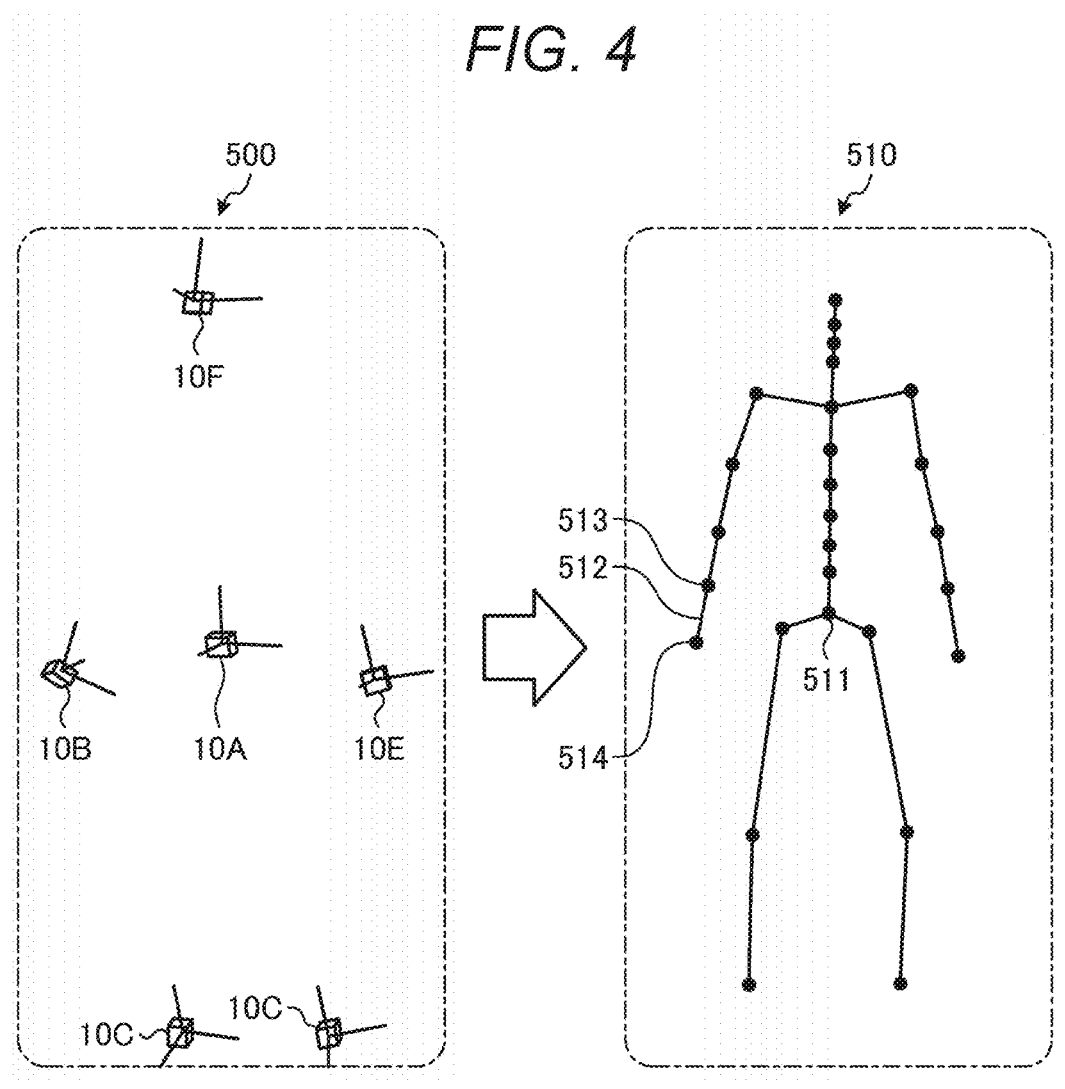
FIG. 4 is a diagram illustrating a specific example of generation of inertial skeleton data according to the embodiment.

Here, processing executed by the information processing apparatus 100 will be described in detail with reference to FIG. 4 and the subsequent drawings. FIG. 4 is a diagram illustrating a specific example of generation of the inertial skeleton data 20 according to the embodiment.

As illustrated in the left diagram of FIG. 4, the information processing apparatus 100 acquires attached part information 500 including the position information and the posture information of the attached parts to which the sensor devices 10A to 10F are attached on the basis of the sensor data.

Subsequently, the information processing apparatus 100 acquires inertial skeleton data 510 including the position information and the posture information of each part in the skeleton structure on the basis of the attached part information 500 as illustrated in the right diagram of FIG. 4. As illustrated in FIG. 4, the inertial skeleton data 510 includes not only information of an attached part 511 corresponding to the sensor device 10A and an attached part 514 corresponding to the sensor device 10B but also information of a non-attached part 513. This is implemented by the information processing apparatus 100 supplementing a skeleton between the attached part and the non-attached part on the basis of skeleton information of the human, and reflecting supplemented information in the inertial skeleton data 510.

Note that the inertial skeleton data 510 can include bone information (position information, posture information, and the like) in addition to the information of the parts. In the example illustrated in FIG. 4, the inertial skeleton data 510 may include information of a bone 512 between the attached part 514 and the non-attached part 513. That is, the information processing apparatus 100 can specify bone information among parts on the basis of the position information and the posture information of the parts in the skeleton structure. For such processing, the technology described in Patent Document 1 described above may be used.

Next, processing of generating the corrected skeleton data performed by the information processing apparatus 100 will be described with reference to FIG. 5.

Figure 5:
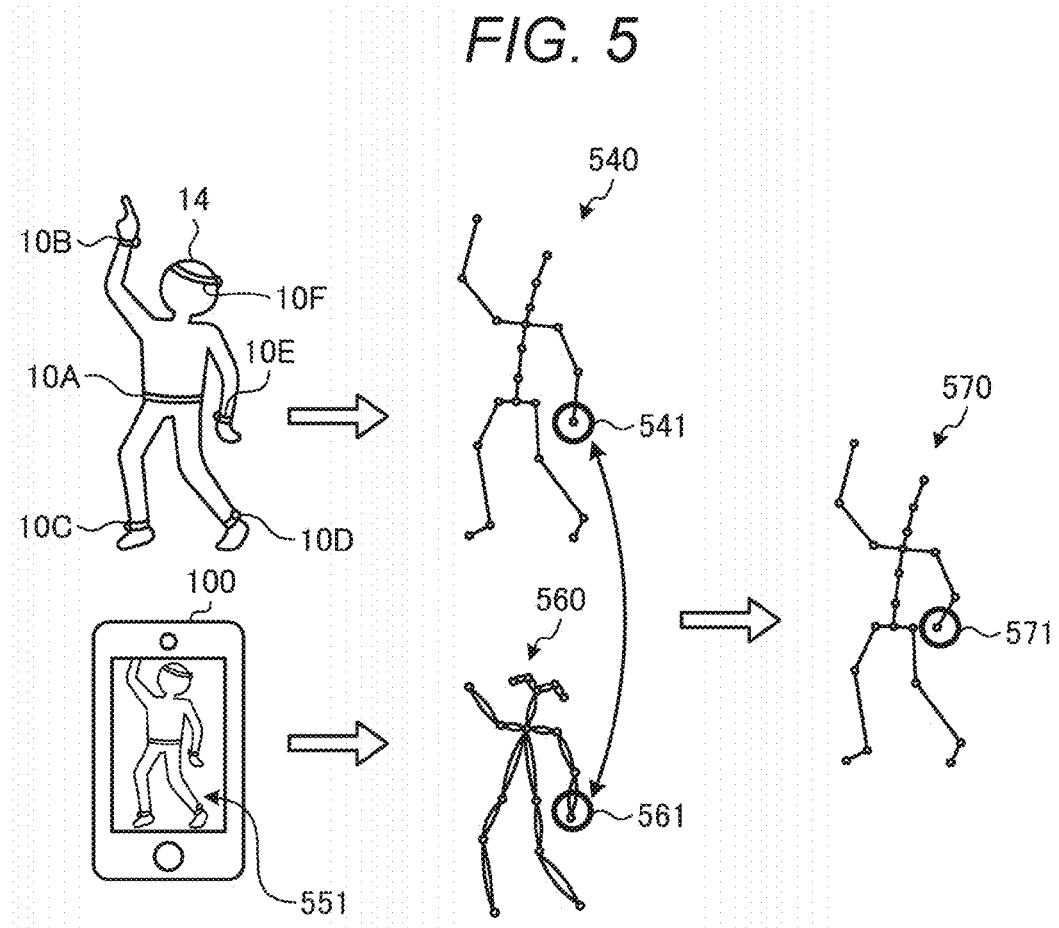
FIG. 5 is a diagram (1) illustrating an example of generation of corrected skeleton data.

FIG. 5 is a diagram (1) illustrating an example of generation of the corrected skeleton data. In FIG. 5, the information processing apparatus 100 acquires data output from the sensor devices 10A to 10F attached to the user 14 via communication such as Bluetooth (registered trademark), and generates inertial skeleton data 540 on the basis of the acquired sensor data. Furthermore, the information processing apparatus 100 generates optical skeleton data 560 on the basis of the image information of the user 14 imaged by the camera included in its own apparatus.

In the example illustrated in FIG. 5, in an image 551 captured by the camera, the joint of the left hand of the user 14 falls within an angle of view. Therefore, the information processing apparatus 100 can generate the optical skeleton data 560 including position information 561 that is an absolute position of the left hand.

In this case, the information processing apparatus 100 corrects the inertial skeleton data 20 by applying the position 561 of the left hand joint of the optical skeleton data 22 to position information 541 of the left hand joint of the inertial skeleton data 540.

Through the correction processing, the information processing apparatus 100 generates corrected skeleton data 570 in which position information 571 of the left hand joint is corrected. As described above, the information processing apparatus 100 can generate the corrected skeleton data 570 with high accuracy by correcting the inertial skeleton data 540 using an advantage of the optical skeleton data 560 in which the accurate absolute position information of the end joint can be known.

Figure 6:
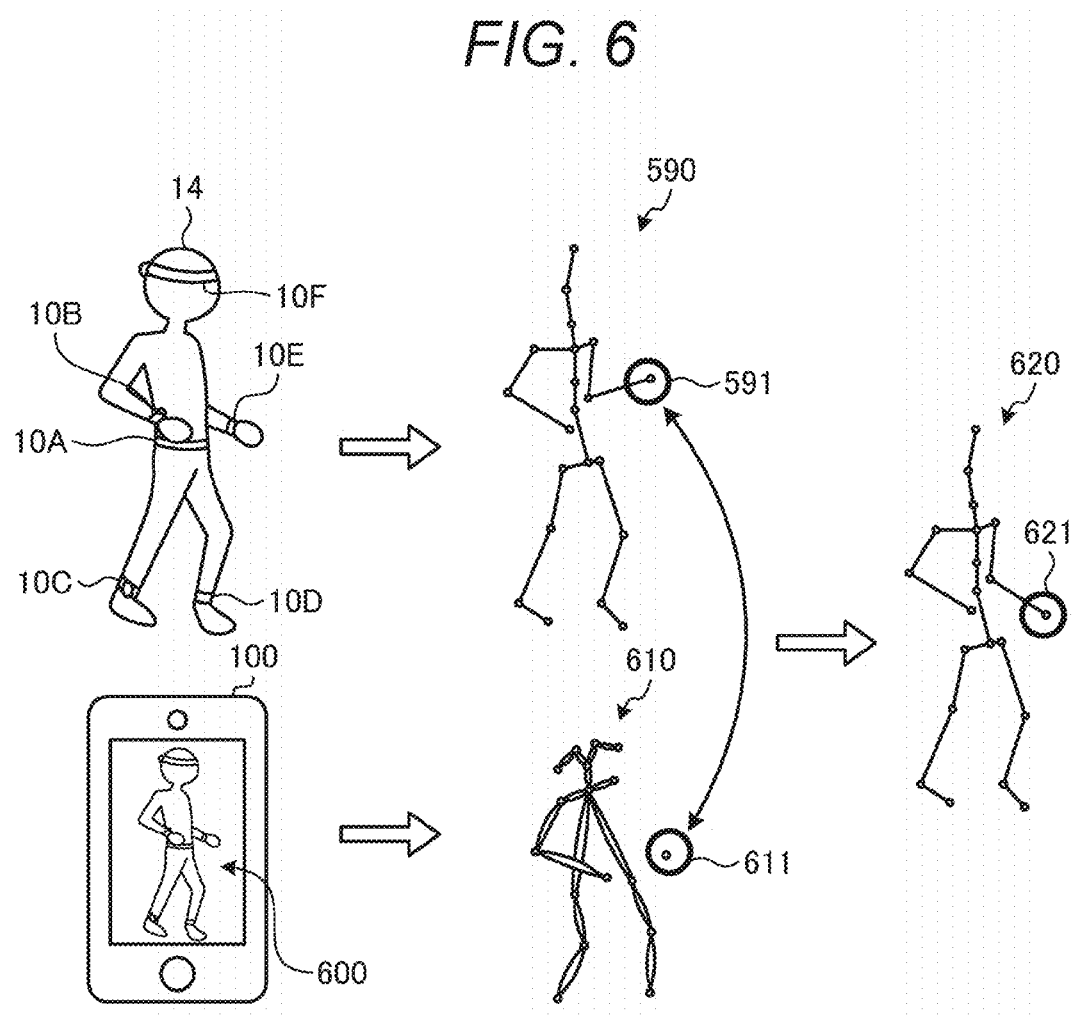

Next, another example of the processing of generating the corrected skeleton data will be described with reference to FIG. 6. FIG. 6 is a diagram (2) illustrating an example of generation of the corrected skeleton data. FIG. 6 illustrates generation processing in a case where, when the user 14 is imaged, the position of an end joint is not imaged well because a part of the body is hidden in another part (referred to as self occlusion or the like).

Similarly to FIG. 5, the information processing apparatus 100 acquires the sensor data from the sensor devices 10A to 10F attached to the user 14, and generates inertial skeleton data 590. Since the inertial skeleton data 590 is generated on the basis of the data acquired by the sensor device 10 attached to a part of the body, the end may be shifted. In the example of FIG. 6, a shift from the actual left hand end of the user 14 occurs at a left hand end position 591 of the user 14 in the inertial skeleton data 590.

Furthermore, the information processing apparatus 100 generates optical skeleton data 610 on the basis of an image 600 obtained by imaging the user 14 with the camera. In the optical skeleton data 610, a left hand end position 611 of the user 14 is relatively accurately reflected as compared to the inertial skeleton data 590. On the other hand, in the example of FIG. 6, the left elbow, which is an elbow joint of the user 14, is not included in the image 600 due to self occlusion. Therefore, the optical skeleton data 610 lacks some information corresponding to the elbow joint of the user 14.

In this case, the information processing apparatus 100 corrects the inertial skeleton data 590 on the basis of the position information of the left hand end position 611 in the optical skeleton data 610, and recalculates the position of the left elbow by a method such as inverse kinematics (IK) using a corrected result. Then, the information processing apparatus 100 generates corrected skeleton data 620 reflecting a recalculated result. The corrected skeleton data 620 includes a left hand end position 621 accurately reflecting the position acquired by the optical skeleton data 610, and the position of the left elbow is recalculated on the basis of the left hand end position 621, so that the position accurately reflecting the movement of the user 14 is obtained.

As described above, even if a part of feature points in the optical skeleton data 610 is lost due to self occlusion, the information processing apparatus 100 can generate the corrected skeleton data 620 with high accuracy by combining the optical skeleton data with the inertial skeleton data 590.

Figure 7:
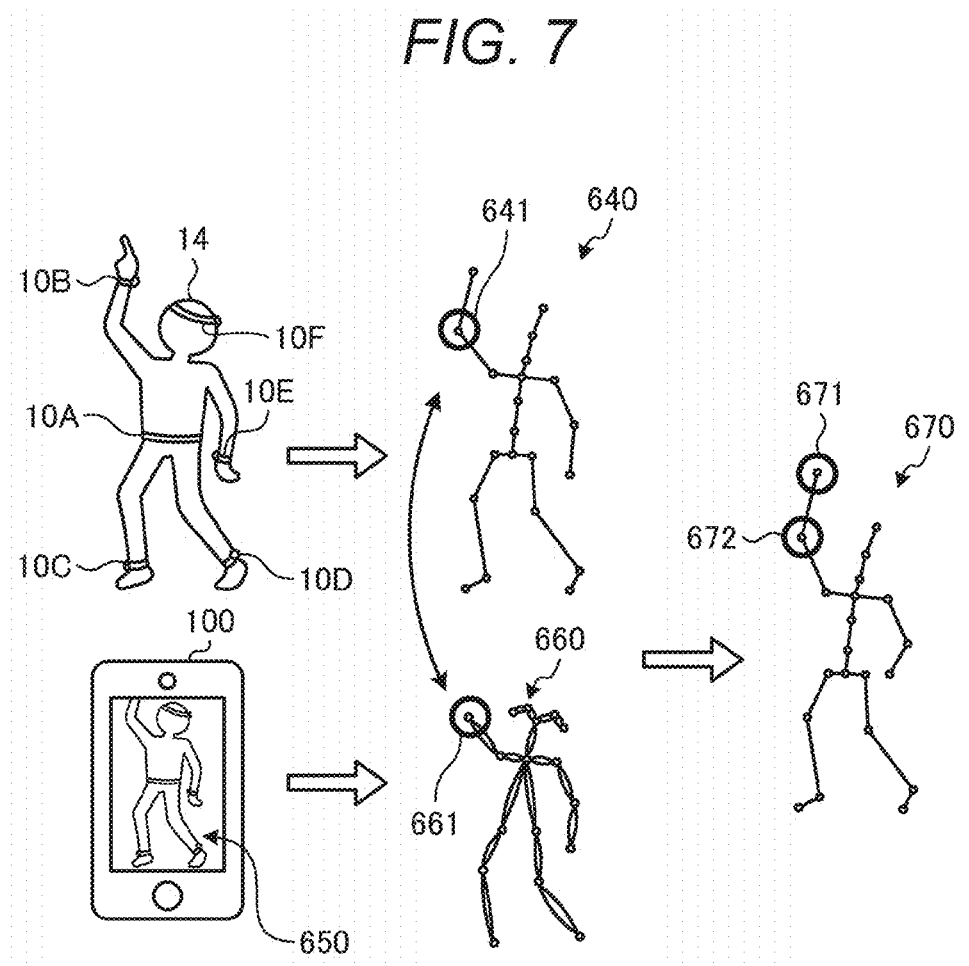
FIG. 7 is a diagram (3) illustrating an example of generation of corrected skeleton data.

Next, another example of the processing of generating the corrected skeleton data will be described with reference to FIG. 7. FIG. 7 is a diagram (3) illustrating an example of generation of corrected skeleton data. FIG. 7 illustrates generation processing in a case where the position of an end joint is not imaged well because a part of the body is out of the angle of view when the user 14 is imaged.

Similarly to FIG. 7, the information processing apparatus 100 acquires the sensor data from the sensor devices 10A to 10F attached to the user 14, and generates inertial skeleton data 640. Since the inertial skeleton data 640 is generated on the basis of the data acquired by the sensor device 10 attached to a part of the body, skeleton data between sensors may be shifted. In the example of FIG. 7, in the inertial skeleton data 640, a right elbow position 641 of the user 14 is shifted from the actual position of the right elbow of the user 14.

Furthermore, the information processing apparatus 100 generates optical skeleton data 660 on the basis of an image 650 obtained by imaging the user 14 with the camera. In the optical skeleton data 660, since the skeleton is estimated on the basis of the image 650 obtained by actually imaging the user 14, a right elbow position 661 of the user 14 is relatively accurately reflected as compared with the inertial skeleton data 640. Meanwhile, since the right hand end of the user 14 is out of the angle of view, the optical skeleton data 660 lacks some information corresponding to the right hand end of the user 14.

In this case, the information processing apparatus 100 corrects the inertial skeleton data 640 on the basis of the position information of the right elbow position 661 in the optical skeleton data 660, and recalculates the position of the right hand end using a corrected result. Then, the information processing apparatus 100 generates corrected skeleton data 670 reflecting a recalculated result. The corrected skeleton data 670 includes a right elbow position 672 accurately reflecting the position acquired by the optical skeleton data 660, and a right hand end position 671 recalculated on the basis of the right elbow position 672 is also a position accurately reflecting the movement of the user 14.

Figure 8:
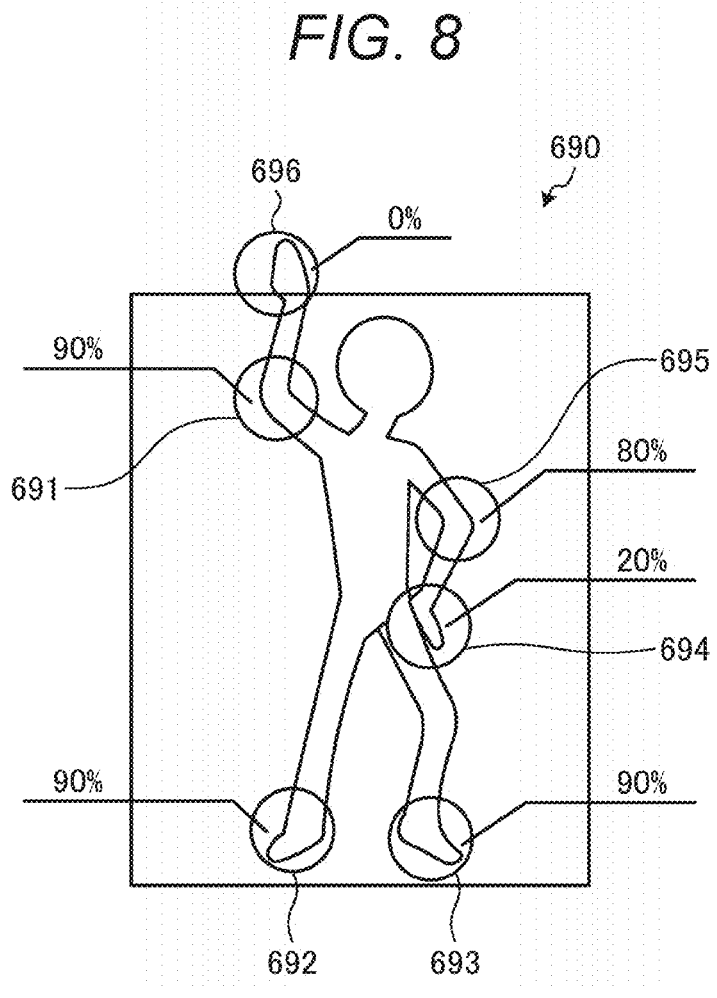
FIG. 8 is a diagram (1) illustrating an outline of a correction algorithm.

Next, a correction algorithm using the degree of reliability of the optical skeleton data by the camera will be described with reference to FIGS. 8 and 9. FIG. 8 is a diagram (1) illustrating an outline of the correction algorithm.

The information processing apparatus 100 estimates, for the position information (for example, an end or an intermediate joint) as a correction target of the skeleton data, the degree of reliability of each position information in the image information serving as a source of the optical skeleton data, and determines whether or not to correct the position. For example, when the degree of reliability is lower than a predetermined threshold, the information processing apparatus 100 does not perform correction using the optical skeleton data with respect to the position information as a correction target of the inertial skeleton data. On the other hand, when the degree of reliability is higher than a predetermined threshold, the information processing apparatus 100 generates the corrected skeleton data by using the position information obtained from the optical skeleton data in preference to the inertial skeleton data. Note that various known techniques can be applied to the processing of estimating the degree of reliability indicating how reliable each position is when the human is imaged by the camera.

In the example illustrated in FIG. 8, the information processing apparatus 100 estimates the degree of reliability of each of a right elbow position 691, a right foot end position 692, a left foot end position 693, a left hand end position 694, a left elbow position 695, and a right hand end position 696 in an image 690 obtained by imaging the user 14. Note that the information processing apparatus 100 may estimate each piece of position information by its own apparatus, or may acquire the degree of reliability of each piece of position information estimated by another apparatus and use an acquired numerical value.

For example, the information processing apparatus 100 estimates relatively high degrees of reliability for the right elbow position 691, the right foot end position 692, the left foot end position 693, and the left elbow position 695 that are clearly included in the angle of view of the camera. On the other hand, the information processing apparatus 100 estimates a relatively low degree of reliability for the left hand end position 694 partially out of the angle of view of the camera. Furthermore, the information processing apparatus 100 determines that the degree of reliability for the right hand end position 696 completely out of the angle of view of the camera is 0.

In the example of FIG. 8, for the right elbow position 691, the right foot end position 692, the left foot end position 693, and the left elbow position 695 for which relatively high degrees of reliability are estimated, the information processing apparatus 100 performs correction processing using the position information to calculate the posture information, and generates the corrected skeleton data. At this time, the information processing apparatus 100 may correct the position information using the estimated degrees of reliability as correction coefficients. Furthermore, in a case where there is a difference in the degrees of reliability between the end joint and the intermediate joint, the information processing apparatus 100 may perform correction, first applying a higher degree of reliability.

Meanwhile, the information processing apparatus 100 generates the corrected skeleton data using the position information calculated on the basis of the position information acquired by the sensor device 10, for example, without using the left hand end position 694 and the right hand end position 696 with low degrees of reliability for the correction processing.

Next, another example of the correction algorithm using the degree of reliability of the optical skeleton data by the camera will be described with reference to FIG. 9. FIG. 8 illustrates an example of generating the corrected skeleton data on the basis of the position information of each part of the user 14 captured by the camera. However, depending on the movement of the user 14, an erroneous degree of reliability may be estimated for the position information of each part of the user 14 captured by the camera. In FIG. 9, correction processing in such a case will be described. FIG. 9 is a diagram (2) illustrating an outline of the correction algorithm.

Figure 9:
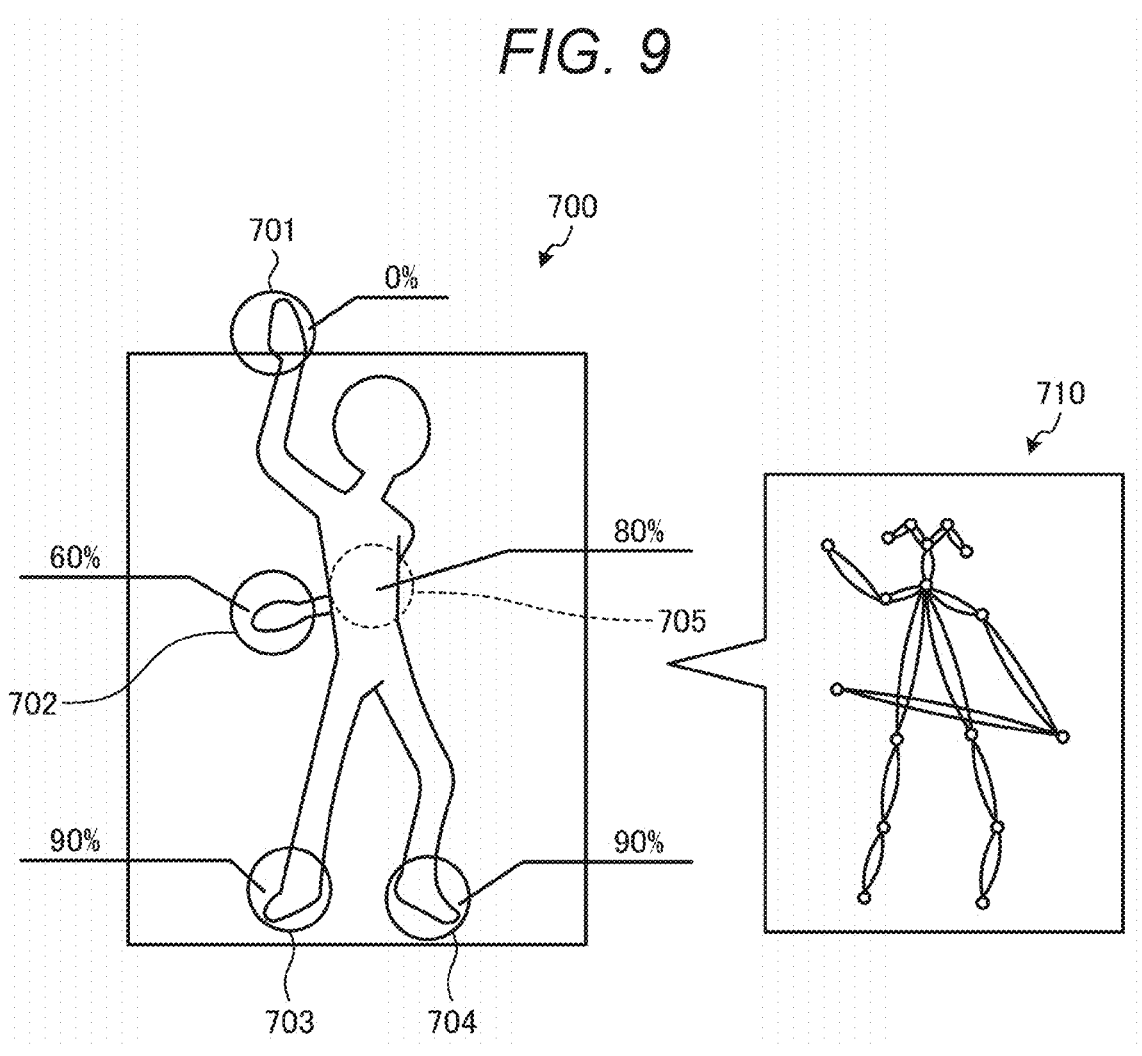
FIG. 9 is a diagram (2) illustrating an outline of a correction algorithm.

In the example of FIG. 9, the information processing apparatus 100 estimates relatively high degrees of reliability for a right foot end position 703, a left foot end position 704, and a left elbow position 705 in an image 700. Meanwhile, the information processing apparatus 100 estimates a relatively low degree of reliability for a left hand end position 702. Furthermore, the information processing apparatus 100 determines that the degree of reliability for a right hand end position 701 completely out of the angle of view of the camera is 0.

Note that optical skeleton data 710 illustrated in FIG. 9 indicates the skeleton data generated on the basis of the degree of reliability in the image 700. As illustrated in FIG. 9, the optical skeleton data 710 may be generated significantly different from the movement of the user 14 in the image 700. This is because the processing of estimating the degree of reliability and the processing of generating the skeleton data on the basis of the degree of reliability are not performed using only the image at the moment captured by the camera, but also using information obtained by estimating the next movement of the user 14 along the time series. In the example illustrated in FIG. 9, the movement (for example, the movement of the user 14 corresponding to the image 690 of FIG. 8) of the user 14 immediately before the image 700 is captured has an influence. Therefore, it is assumed that the information processing apparatus 100 erroneously estimates the numerical value of the degree of reliability and generates the skeleton data along the left elbow position 695 in FIG. 8.

In this case, although the skeleton data is generated along the numerical value of the degree of reliability, the actual position of the left elbow of the user 14 and the position of the left elbow in the skeleton data are greatly different. Then, the information processing apparatus 100 refers to the result of the inertial data acquired by the sensor device 10, and in a case where the position of the left elbow in the skeleton data is different from the position of the left elbow estimated from the inertial data by a predetermined distance or more, the information processing apparatus 100 determines not to perform the correction processing based on the image 700. That is, the information processing apparatus 100 can perform appropriate correction processing by removing an exceptional value obtained from the image 700 using the posture information obtained by the inertial skeleton data.

As described above, in a case of attempting to generate the skeleton data with the appearance of the user 14 on the basis of the image 700, the information processing apparatus 100 regards another part of the body as an arm even in a case where the left elbow is hidden, and forcibly estimates the skeleton to generate the skeleton data in some cases. However, when generating the skeleton data on the basis of such information, the difference from the inertial skeleton data is observed to be much larger than usual. Therefore, the information processing apparatus 100 can exclude the position of the left elbow as an outlier.

As described above, the calculation unit 166 according to the information processing apparatus 100 generates the corrected skeleton data by estimating the degree pf reliability regarding the optical skeleton data and performing correction according to the degree of reliability. That is, the information processing apparatus 100 can improve the accuracy of the skeleton data to be generated by generating the corrected skeleton data while compensating for contradiction occurring in either the inertial skeleton data or the optical skeleton data.

1-4. Processing Procedure of Information Processing System According to Embodiment Next, a processing procedure by the information processing system 1 including the information processing apparatus 100 will be described with reference to FIGS. 10 to 13. Note that, hereinafter, a series of functional configurations for the information processing apparatus 100 to obtain the inertial skeleton data on the basis of the inertial data acquired from the sensor device 10 may be referred to as an inertial motion capture system. Furthermore, a series of functional configurations for the information processing apparatus 100 to obtain the optical skeleton data on the basis of the image information (optical data) acquired from the camera may be referred to as a camera motion capture system.

Figure 10:
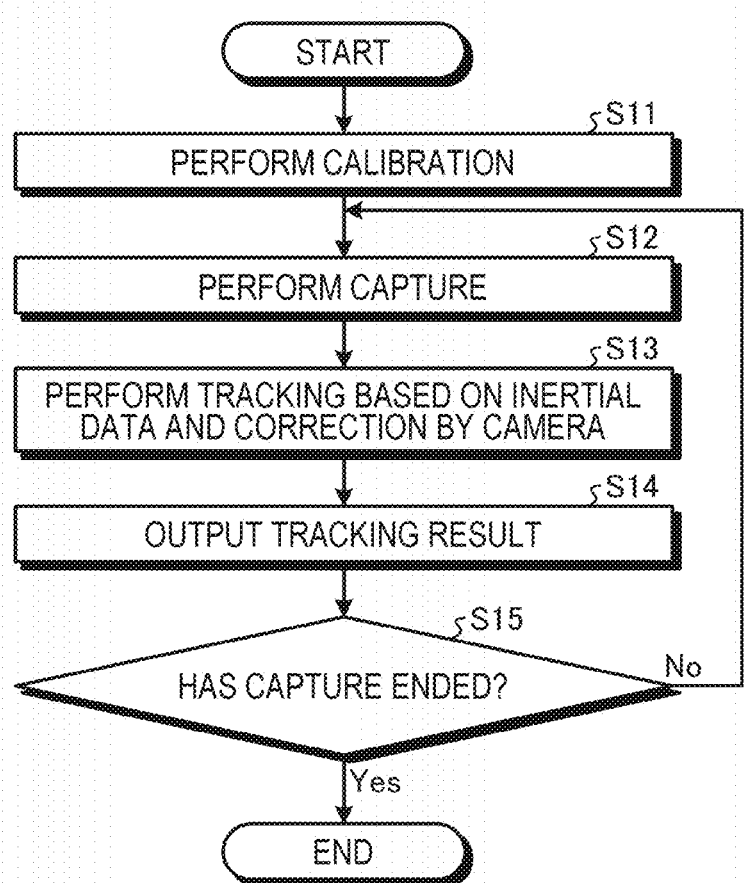
FIG. 10 is a flowchart illustrating an outline of an overall procedure when motion capture is executed according to the embodiment.

FIG. 10 is a flowchart illustrating an outline of an overall procedure when motion capture is executed according to the embodiment. Specifically, FIG. 10 illustrates a flow of the entire procedure when the information processing apparatus 100 executes motion capture of the user 14 using the inertial motion capture system and the camera motion capture system.

As illustrated in FIG. 10, prior to capture, the information processing apparatus 100 performs calibration for aligning coordinate systems of the inertial motion capture system and the camera motion capture system (step S11). Details of the calibration will be described below.

Thereafter, the information processing apparatus 100 starts capture (step S12). Specifically, the information processing apparatus 100 generates the inertial skeleton data, using the inertial data acquired from the sensor device 10 attached to the user 14, using the inertial motion capture system. Furthermore, the information processing apparatus 100 starts imaging of the user 14 by the camera 140, and generates the optical skeleton data on the basis of the acquired image information.

Then, the information processing apparatus 100 corrects the movement of the user 14 on the basis of the image information acquired from the camera 140 while continuing tracking of the movement of the user 14 based on the inertial data (step S13). For example, the information processing apparatus 100 performs such correction for each frame rate of the camera 140.

Then, the information processing apparatus 100 outputs a tracking result (step S14). Specifically, the information processing apparatus 100 calculates the posture information (that is, the corrected skeleton data) corrected every predetermined time corresponding to the frame rate, and outputs the calculated posture information.

Thereafter, the information processing apparatus 100 determines whether or not the capture of the user 14 has ended (step S15). In a case where the capture has not ended (step S15; No), the information processing apparatus 100 continues the capture (step S12). On the other hand, in a case where the capture has ended (step S15; Yes), the information processing apparatus 100 terminates the entire processing.

Next, calibration for aligning references of the inertial data and the optical data, which are a premise before the above-described correction processing is performed, will be described with reference to FIGS. 11 and 12.

Figure 11:
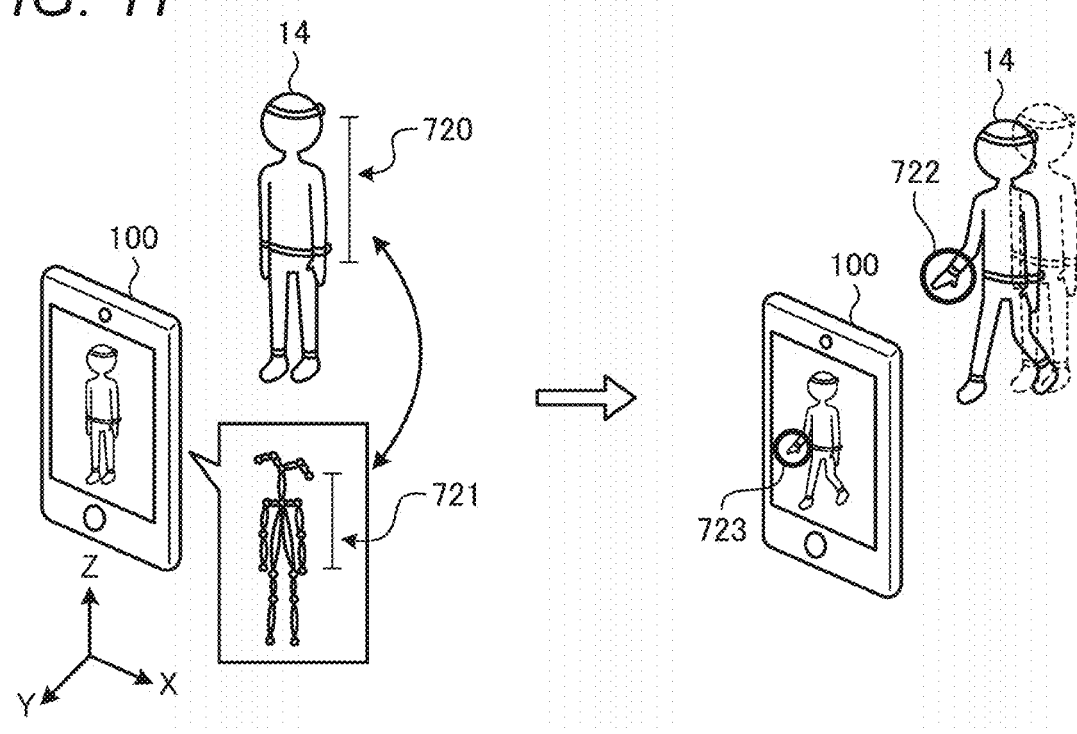
FIG. 11 is a diagram for describing calibration processing between an inertial motion capture system and a camera motion capture system.

FIG. 11 is a diagram for describing calibration processing between the inertial motion capture system and the camera motion capture system. The inertial skeleton data obtained by the inertial motion capture system and the optical skeleton data obtained by the camera motion capture system are different in size and coordinate system, and thus cannot be used as they are for the correction processing. Therefore, prior to the correction processing, the information processing apparatus 100 performs calibration so as to align the coordinate systems of the two systems.

Specifically, as calibration, the information processing apparatus 100 calculates predetermined parameters so that pieces of the size and joint information of the inertial skeleton data and the optical skeleton data match. For example, the information processing apparatus 100 calculates an axis transformation matrix between the camera motion capture system and the inertial motion capture system. Note that, when depth information cannot be acquired as a function of the camera, the information processing apparatus 100 may calculate an inter-joint distance to be used as a reference of a scale (size) in the two systems instead of the axis transformation matrix.

Specific implementation of the calibration will be described with reference to FIG. 11. First, the information processing apparatus 100 images the user 14 at the start of the inertial capture system. For example, the information processing apparatus 100 images an upright posture (generally referred to as "N pose" or the like) of the user 14.

At this time, since the coordinate system of the inertial system includes a back muscle direction of the user 14 (a z axis of coordinate axes illustrated in FIG. 11) and a front direction of the user 14 (a y axis of the coordinate axes), the information processing apparatus 100 adjusts the coordinate system of the camera to the directions according to an operation or the like by an operator. For example, the information processing apparatus 100 matches a distance 720 from the head to the waist of the user 14, which is a reference scale, and a distance 721 corresponding to the distance 720 on the image. Specifically, the information processing apparatus 100 can align the size and coordinate systems of the two systems by calculating the axis transformation matrix, which is the parameters for matching reference scales between the systems. After the calibration, even if the user 14 moves in a direction including a depth direction (an x axis of the coordinate axes), the information processing apparatus 100 can align information between the two systems by applying the calculated axis transformation matrix.

Note that, even in a case where the camera included in the information processing apparatus 100 is a camera that cannot acquire the depth direction, such as an RGB monocular camera, the information processing apparatus 100 can adjust the bone estimation result by setting the distance of joints (for example, from the head to the waist of the user 14) as scale reference information and using the distance information of joints as scale factors when the user 14 moves in the depth direction.

By performing such calibration at predetermined timing (for example, for each frame of imaging by the camera), the information processing apparatus 100 can perform the correction processing, the avatar generation processing, and the like in real time.

Note that the information processing apparatus 100 may use the image information to determine whether or not the calibration has been accurately performed at the time of executing the calibration. Success or failure of the calibration can be checked by, for example, the user 14 being imaged by the camera walks toward a camera side one step. At this time, the information processing apparatus 100 performs determination based on the image information. Specifically, as illustrated in the right diagram of FIG. 10, the information processing apparatus 100 observes that a right hand position 722 of the user 14 that should not move has moved. In a case where it can be determined from information of a camera image that the right hand of the user 14, which should not move when the user walks one step forward (for example, in a case where it is determined that a right hand position 723 in the captured image information has substantially moved from a predetermined position), the information processing apparatus 100 may determine that the calibration does not hold, and issue a warning or the like requesting the user 14 to redo again, for example.

A calibration procedure will be described with reference to FIG. 12. FIG. 12 is a flowchart illustrating a processing procedure of the calibration according to the embodiment.

As illustrated in FIG. 12, the information processing apparatus 100 observes the N pose of a capture target (user 14) (step S21). Specifically, the information processing apparatus 100 images the user 14 taking the N pose.

Subsequently, the information processing apparatus 100 determines whether or not main joints have been estimated by the camera 140 (step S22). Specifically, the information processing apparatus 100 determines whether or not the posture information corresponding to the optical skeleton data has been estimated on the basis of the image information acquired by the camera 140. Note that the main joints correspond to, for example, the positions of the waist and the head of the user 14.

In a case where the main joints have not been estimated by the camera 140 (step S22; No), the information processing apparatus 100 again performs imaging by the camera 140, and adjusts camera parameters and the angle of view so as to be able to estimate the main joints.

On the other hand, in a case where the main joints have been estimated by the camera 140 (step S22; Yes), the information processing apparatus 100 requests a target to perform an action (step S23). For example, the information processing apparatus 100 requests the user 14 to walk one step forward to the camera 140, for example.

In response to such an action, the information processing apparatus 100 determines whether or not the inertial data associated with the action has been acquired without any problem and whether or not there is an abnormality in the main joint estimation by the camera 140 (step S24).

In a case where there is a problem in acquisition of the inertial data associated with the action, or in a case where there is an abnormality in the main joint estimation by the camera 140 (step S24; No), the information processing apparatus 100 adjusts the camera parameters and the angle of view so that no abnormality occurs in the estimation processing and the like, and then requests the target to perform the action again.

On the other hand, in a case where there is no problem in the acquisition of the inertial data associated with the action and there is no abnormality in the main joint estimation by the camera 140 (step S24; Yes), the information processing apparatus 100 refers to the acquired inertial data and the main joint estimation by the camera, and calculates a coordinate transformation matrix and scale factors from relative position information of both the main joints (step S25). With this processing, the calibration ends.

Figure 13:
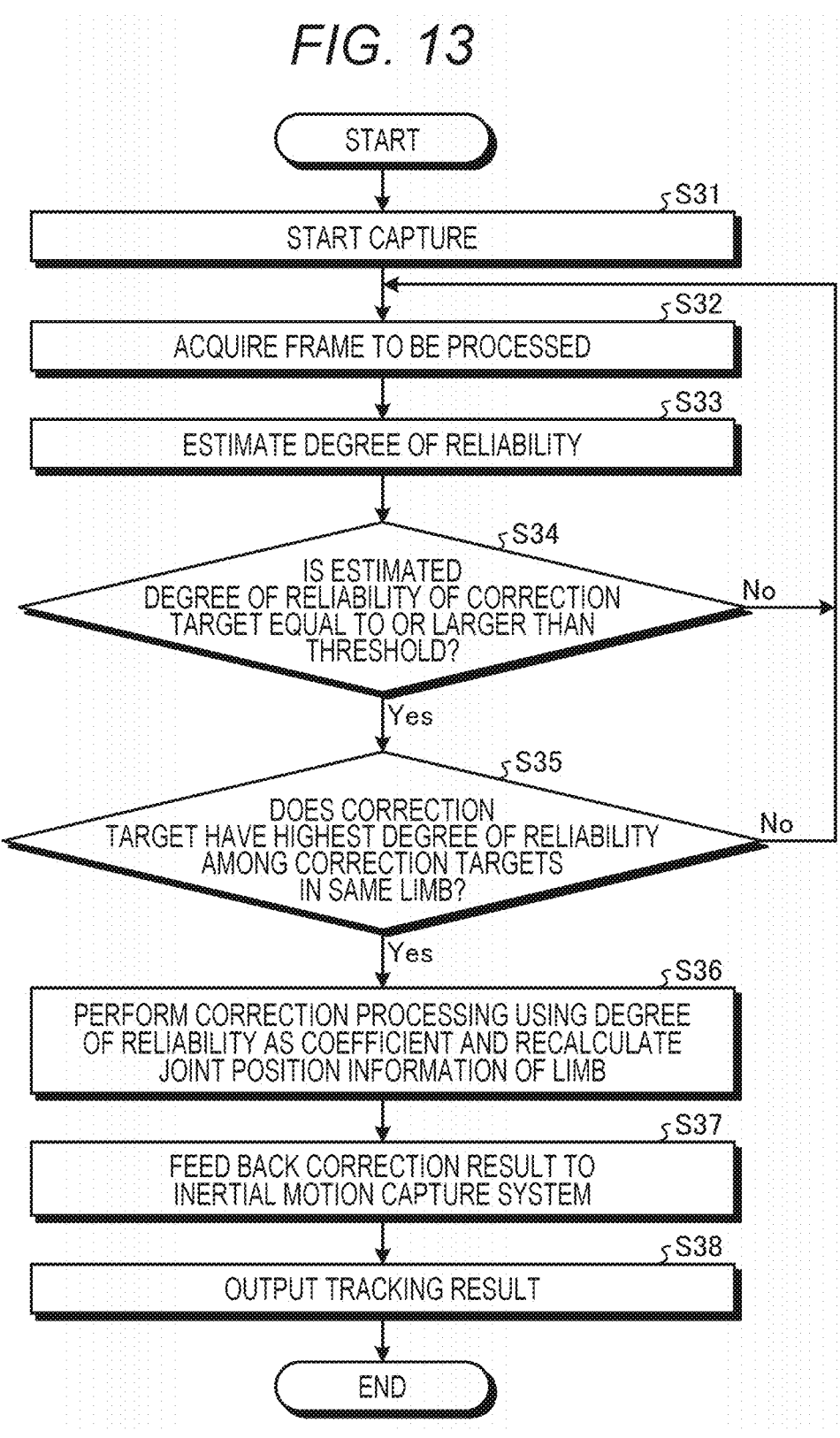
FIG. 13 is a flowchart illustrating a processing procedure of capture according to the embodiment.

Next, a detailed procedure of correction processing in capture will be described with reference to FIG. 13. FIG. 13 is a flowchart illustrating a processing procedure of capture according to the embodiment.

The information processing apparatus 100 starts capturing the target by using the sensor device 10 and the camera 140 (step S31). Then, the information processing apparatus 100 acquires data for one frame to be processed in accordance with the frame rate of imaging by the camera 140 or the like (step S32).

The information processing apparatus 100 estimates the degree of reliability of a portion as a correction target in the image information acquired by the camera 140 (step S33). As illustrated in FIG. 8 and the like, the portion as a correction target is an end, an intermediate joint, or the like of the user 14.

The information processing apparatus 100 determines whether or not the degree of reliability estimated for a certain correction target exceeds a predetermined threshold (step S34). In a case where the degree of reliability does not exceed the predetermined threshold (step S34; No), the information processing apparatus 100 determines that the correction target has some problem, does not use the correction target, and performs processing for the next frame. Note that, although not illustrated in FIG. 13, the information processing apparatus 100 repeats the determination as to whether or not the degree of reliability exceeds the threshold value as many times as the number of correction targets.

In a case where the degree of reliability exceeds the predetermined threshold (step S34; Yes), the information processing apparatus 100 sets the correction target as a candidate for the correction target and further determines whether or not the correction target has the highest degree of reliability among the correction targets of the same limb (step S35). For the correction target having not the highest degree of reliability (step S35; No), the information processing apparatus 100 does not use the correction target but uses another correction target having the highest degree of reliability.

When the correction target with the highest degree of reliability is selected from the same limb, the information processing apparatus 100 performs the correction processing for the correction target with the degree of reliability as a coefficient, and recalculates joint position information of the limb (step S36). As a result, the information processing apparatus 100 can correct the joint position of the user 14 estimated on the basis of the inertial data to a relatively accurate position captured by the camera 140.

Note that, although the example of FIG. 13 illustrates that the correction is performed using only the correction target with the highest degree of reliability of the limb, the information processing apparatus 100 may perform the correction using not only the correction target with the highest degree of reliability but also a plurality of correction targets.

The information processing apparatus 100 feeds back the recalculated joint position to the inertial motion capture system (step S37). That is, the information processing apparatus 100 calculates the posture information (that is, the corrected skeleton data) obtained as a result of a feedback.

Then, the information processing apparatus 100 outputs the corrected skeleton data that is a tracking result obtained by the calculation (step S38).

Figure 14:
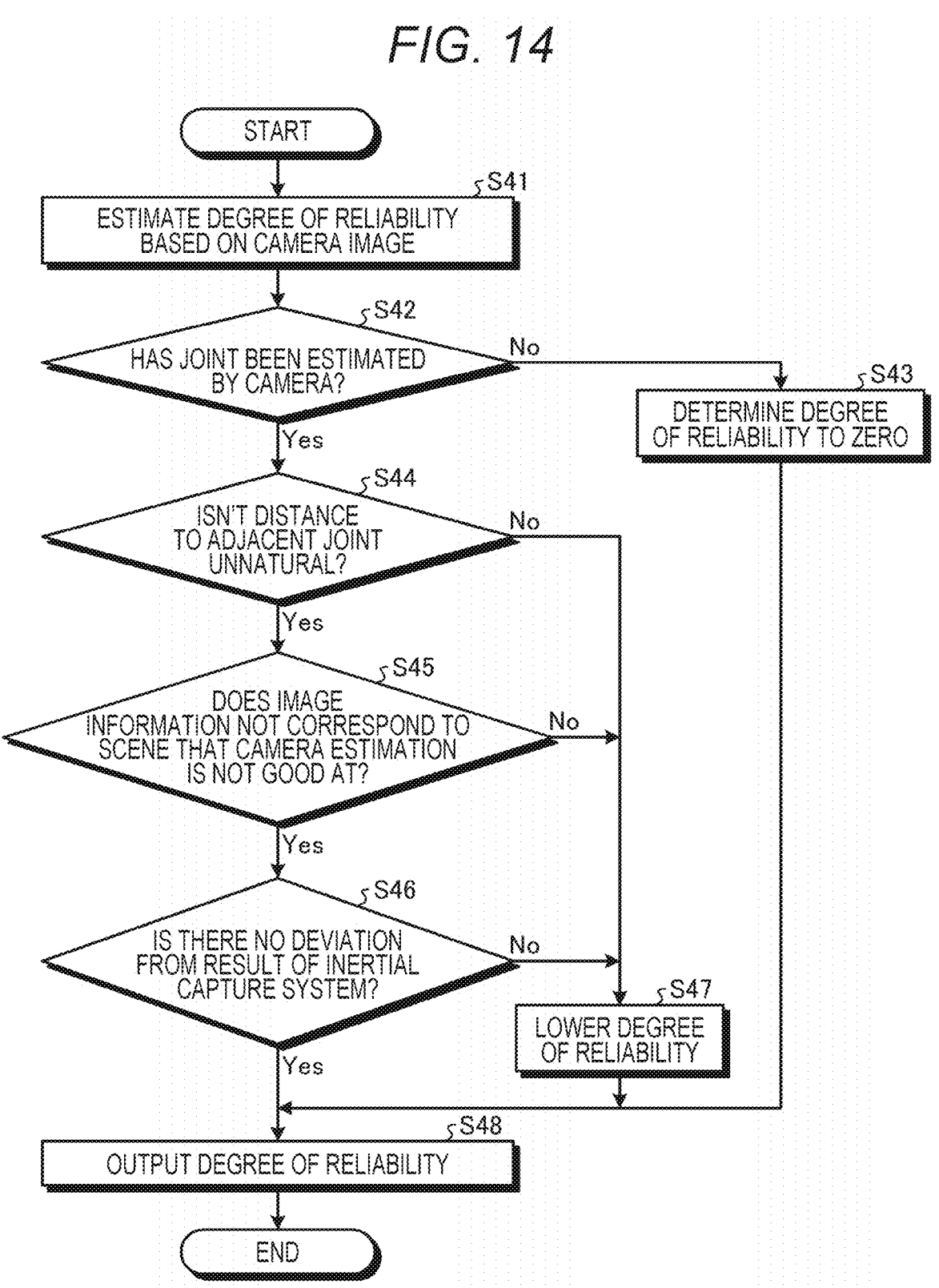
FIG. 14 is a flowchart illustrating a processing procedure of estimation of the degree of reliability according to the embodiment.

The processing of estimating the degree of reliability illustrated in FIG. 13 will be described in more detail with reference to FIG. 14. FIG. 14 is a flowchart illustrating a processing procedure of estimation of the degree of reliability according to the embodiment.

First, the information processing apparatus 100 attempts to estimate the degree of reliability on the basis of the image information captured by the camera 140 (step S41).

At this time, the information processing apparatus 100 determines whether or not the joint to be processed has been estimated by the camera (step S42). For example, the information processing apparatus 100 determines whether the joint to be processed does not fall within the angle of view of the camera 140 or is hidden by self occlusion.

In a case where the joint to be processed cannot be estimated by the camera (step S42; No), the joint is not specified from the camera image in the first place, the information processing apparatus 100 determines that the degree of reliability of the joint to be processed is 0 (step S43).

On the other hand, in a case where it is determined that the estimation by the camera has been performed (step S42; Yes), the information processing apparatus 100 determines whether or not the distance to an adjacent joint is not unnatural (step S44). The distance to an adjacent joint being unnatural refers to, for example, a case where the joint s to be processed are observed at positions exceeding a predetermined threshold at the time of calibration or in comparison with the previous frame in time series. For example, the joint positions corresponding to the optical skeleton data 710 in FIG. 9 are in a situation where the joint positions are estimated as unnatural positions.

In a case where it is determined that the distance to the adjacent joint is not unnatural (step S44; Yes), it is determined whether or not the image information captured by the camera 140 corresponds to a scene that the estimation by the camera is not good at (step S45). The scene that the estimation by the camera is not good at means, for example, a situation determined that it is difficult to grasp the target as the ability of the camera, such as the target moving at a very high speed or the target being too close or too far from the camera. The information processing apparatus 100 may acquire information indicating that imaging is difficult from a processing unit of the camera and perform the determination in step S45 on the basis of the acquired information, or may perform the determination by its own apparatus. For example, the camera may transmit, to the information processing apparatus 100, information of a possibility that the camera cannot appropriately image the moving body on the basis of environment information of when imaging the moving body. For example, the camera determines that the environment information at the time of imaging is not appropriate in a case where there is a lot of noise in an imaging environment (including many objects detected as noise such as rain or snow), in a case where part of face detection or joint detection for the moving body is not successful, in a case where a target to which a focal length is to be adjusted cannot be clearly specified, or the like. Then, the camera transmits information indicating that the environment information at the time of imaging is not appropriate to the information processing apparatus 100 together with the image information. In a case of acquiring such information, the information processing apparatus 100 determines that the image information corresponds to the scene that the estimation by the camera is not good at. Alternatively, the information processing apparatus 100 determines the image information corresponds to the scene that the estimation by the camera is not good at in a case where it is not possible to specify what the moving body is or it is not possible to specify information required for skeleton detection such as a face or a joint of the moving body in the acquired image information. That is, the information processing apparatus 100 may determine that the image information corresponds to the scene that the estimation by the camera is not good at on the basis of reliability (for example, an index value indicating whether or not the optical skeleton data has been appropriately generated) of the skeleton information of the moving body obtained from the image information.

In a case where it is determined that the image information does not correspond to the scene that the estimation by the camera is not good at (step S45; Yes), the information processing apparatus 100 determines whether or not there is a deviation exceeding a predetermined value between the result of the inertial capture system and the joint position estimated by the camera (step S46).

In a case where there is no deviation from the result of the inertial capture system (step S46; Yes), the information processing apparatus 100 outputs the degree of reliability estimated in step S41 as it is (step S48).

On the other hand, in a case where there is a deviation from the result of the inertial capture system (step S46; No), or in a case where it is determined that the distance to the adjacent joint is unnatural (step S44; No) or in a case where it is determined that the image information corresponds to the scene that the estimation by the camera is not good at (step S45; No), the information processing apparatus 100 lowers the degree of reliability according to each condition (step S47). A calculation method of lowering the degree of reliability is arbitrary, and for example, the calculation may be performed on the basis of a parameter set in advance for each condition, or the degree of reliability may be lowered according to a degree in a condition (for example, a parameter indicating unnaturalness of the joint position is defined in advance, and an appropriate parameter is used depending on the degree of unnaturalness).

The information processing apparatus 100 performs the processing illustrated in FIG. 14 for all the processing targets included in one frame and calculates the degree of reliability. Then, the information processing apparatus 100 determines, on the basis of the calculated degree of estimation, matters such as whether or not to perform the correction processing and for which correction target the correction is to be performed.

1-5. Modification of Embodiment (1-5-1. Real-time Processing)

Figures 15, 16:
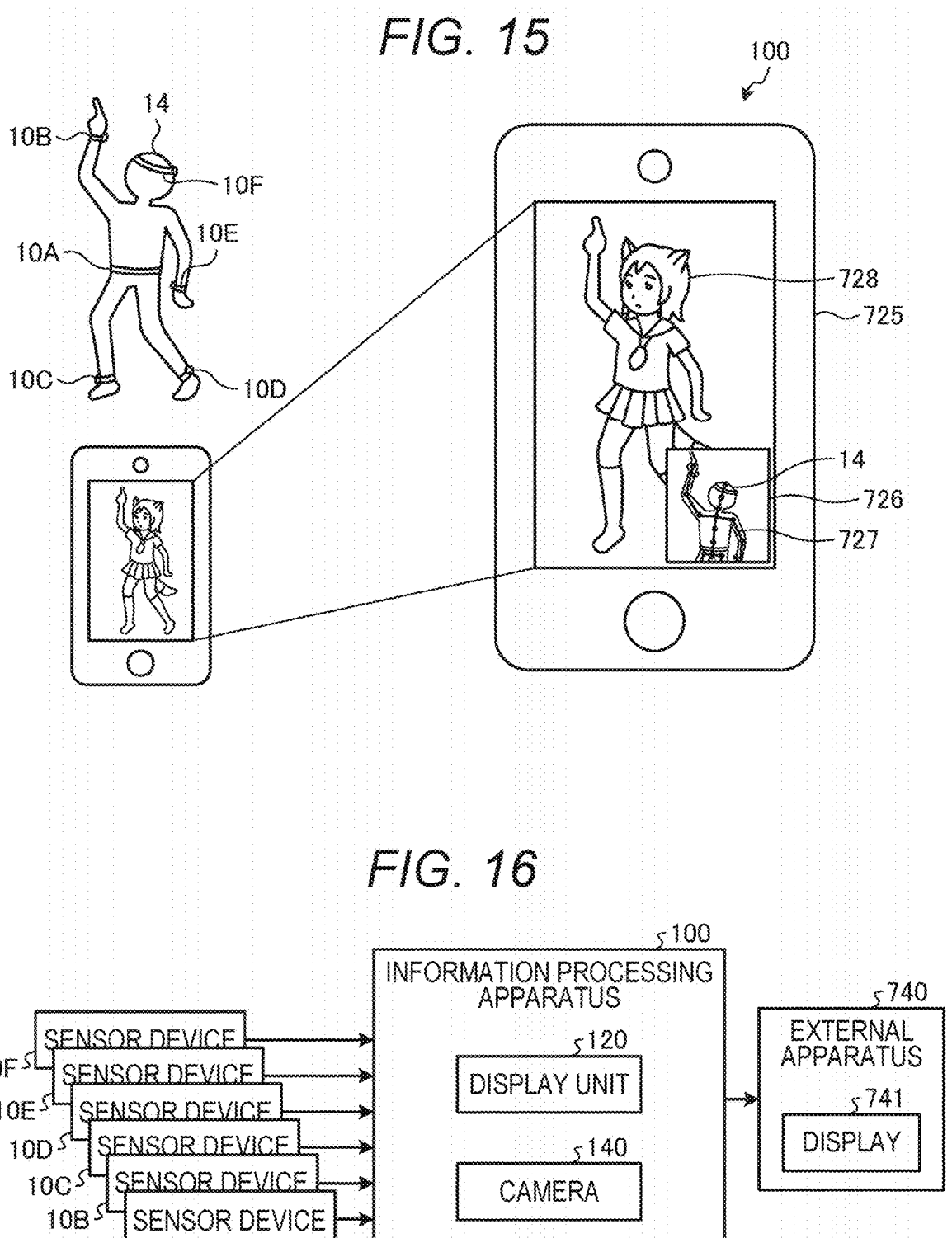
FIG. 15 is a diagram illustrating an outline of information processing according to a first modification.
FIG. 16 is a diagram illustrating a configuration example of a system that executes information processing according to the first modification.

The information processing apparatus 100 of the present disclosure may be accompanied by various modifications to be described below. FIG. 15 is a diagram illustrating an outline of information processing according to a first modification.

FIG. 15 illustrates an example in which, in a case where the information processing apparatus 100 images the user 14, the information processing according to the embodiment is performed in real time, and the captured information is applied to the avatar at the same time as imaging the user 14.

As illustrated in FIG. 15, the user 14 wears the sensor devices 10A to 10F. The information processing apparatus 100 acquires the sensor data from the sensor devices 10A to 10F, and generates the inertial skeleton data of the user 14 using the inertial motion capture system. Furthermore, the information processing apparatus 100 images the user 14 with the camera 140 and generates the optical skeleton data using the optical motion capture system. Then, the information processing apparatus 100 performs the above-described correction processing to generate the corrected skeleton data. Moreover, the information processing apparatus 100 outputs the avatar to a display screen or the like by retargeting the generated corrected skeleton data to the avatar in real time.

For example, as illustrated in FIG. 15, the information processing apparatus 100 displays a display screen 725 with a captured image 726. The display screen 725 includes the captured image 726 indicating how the user 14 is imaged, and skeleton information 727 superimposed and displayed on the user 14 of the captured image 726. Furthermore, the display screen 725 includes an avatar 728 to which the skeleton information 727 has been retargeted. Therefore, a content creator who images the user 14 can apply the movement of the user 14 to the avatar 728 in real time, and can view the state.

Note that, although FIG. 15 illustrates an example in which the information processing apparatus 100 generates the corrected skeleton data on the basis of information of a rear camera, the information processing apparatus 100 may generate the corrected skeleton data 24 on the basis of a camera provided on a display screen 725 side. In this case, the user 14 can check in real time how his/her movement is applied to the avatar 728 at the same time while imaging himself/herself. That is, the information processing apparatus 100 enables the creator to simultaneously distribute the avatar 728 to other users while checking his/her movement, and the like, and thus, it is possible to improve mobility and operability of the content creator.

FIG. 16 illustrates a configuration example of a system in a case of executing information processing according to the first modification. FIG. 16 is a diagram illustrating a configuration example of the system that executes the information processing according to the first modification.

As illustrated in FIG. 16, the information processing apparatus 100 acquires the sensor data from the sensor devices 10A to 10F and the image information from the camera 140 included in its own apparatus, and generates the corrected skeleton data through the above-described information processing.

At this time, the information processing apparatus 100 may display an avatar 728 to which the corrected skeleton data is applied to the display unit 120 included in the its own apparatus. Furthermore, the information processing apparatus 100 may distribute the image information, moving image data, and the like including the avatar 728 to an external apparatus 740 via a network. The external apparatus 740 displays the avatar 728 on a display 741.

(1-5-2. Post-Process Processing)

Figure 17:
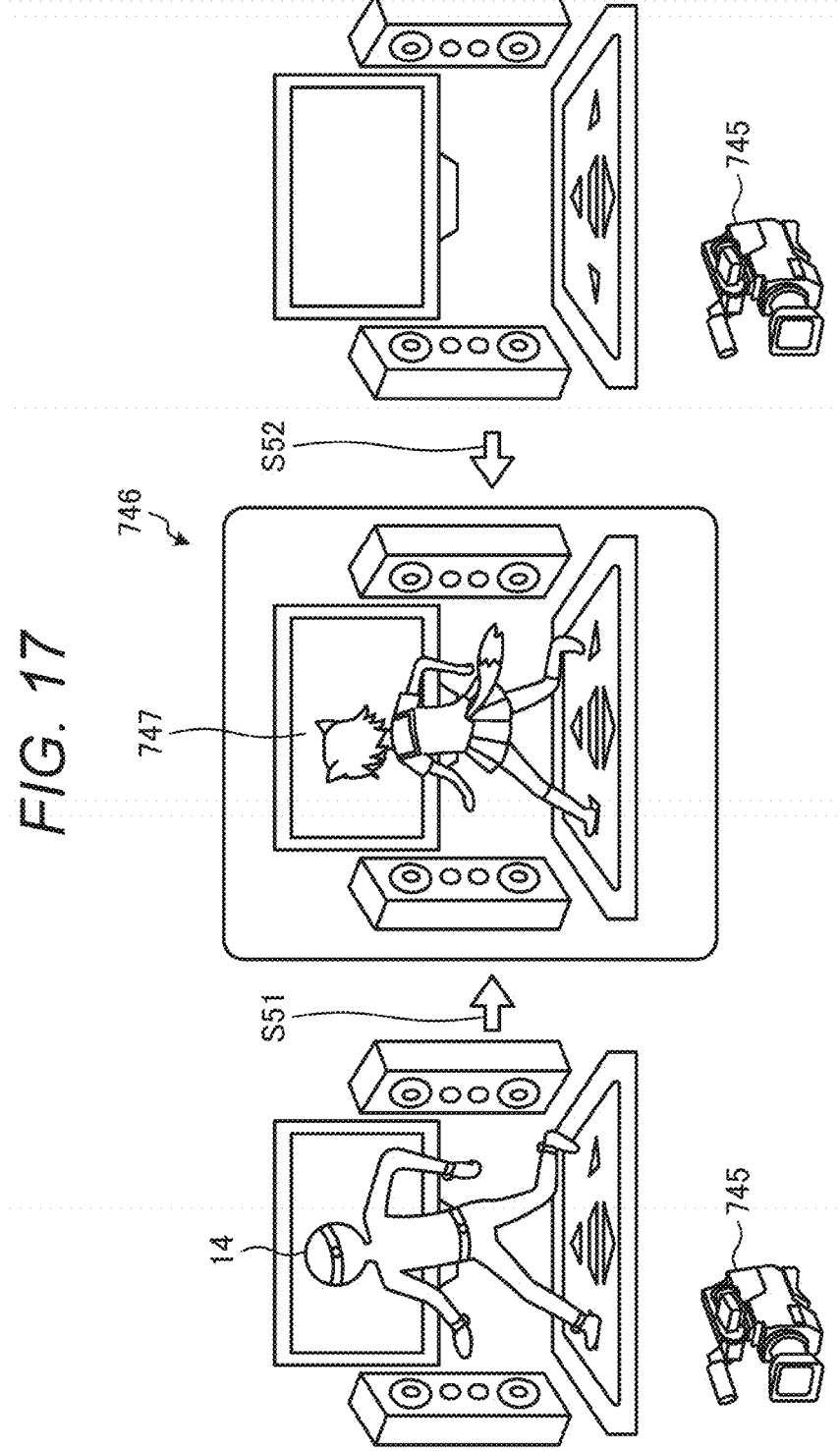
FIG. 17 is a diagram illustrating an outline of information processing according to a second modification.

Next, a second modification will be described with reference to FIG. 17. FIG. 17 is a diagram illustrating an outline of information processing according to the second modification.

In the example illustrated in FIG. 17, processing in which the information processing apparatus 100 generates the corrected skeleton data and then synthesizes the data with a background later (post-process) will be described.

In the example of FIG. 17, the information processing apparatus 100 acquires the image information from a camera 745 that images the user 14, and acquires the inertial data from the sensor device 10 worn by the user 14. The information processing apparatus 100 generates the corrected skeleton data on the basis of the movement of the user 14, and sets the corrected skeleton data as data to be synthesized (step S51).

Furthermore, the camera 745 images a video that serves as a background to which the posture information of the user 14 is applied and the avatar is synthesized in the future, in a state where the user 14 is not present. Background data imaged by the camera 745 is input to the information processing apparatus 100 or a computer that is an information processing apparatus for performing synthesis processing. Then, the information processing apparatus 100 or the computer generates background data for synthesizing the avatar on the basis of the captured image data acquired from the camera 745 (step S52). The background data may be the captured image data itself acquired from the camera 745, or may undergo some processing.

Then, the information processing apparatus 100 or the computer applies the corrected skeleton data to the avatar 747, reproduces the movement of the user 14 on the avatar 747, and applies the background data to the avatar 747, thereby generating a synthesized video 746. That is, the optical data acquisition unit 163 according to the information processing apparatus 100 acquires the image information including the background image from the camera 745 different from the camera 140 included in the information processing apparatus 100. Furthermore, the display control unit 168 according to the information processing apparatus 100 superimposes and displays the avatar on the background image included in the image information.

As described above, the information processing apparatus 100 or the computer may perform post-process processing of performing retargeting after the capture instead of real-time processing of performing retargeting to the avatar 747 at the same time as the capture. Therefore, the information processing apparatus 100 or the computer can implement high-resolution and high-frame-rate video regardless of calculation resources.

In the example of FIG. 17, a virtual camera position at the time of rendering the avatar 747 is aligned with a real camera position (an imaging position of the camera 745 in the example of FIG. 17). Therefore, since a positional relationship between a reference point of the motion capture system and the real camera position coincides in a virtual positional relationship, it is advantageous for rendering the avatar 747. Note that, even in this case, there is a difference in the camera angle of view parameter, and thus the scales of the two are manually changed.

Figure 18:
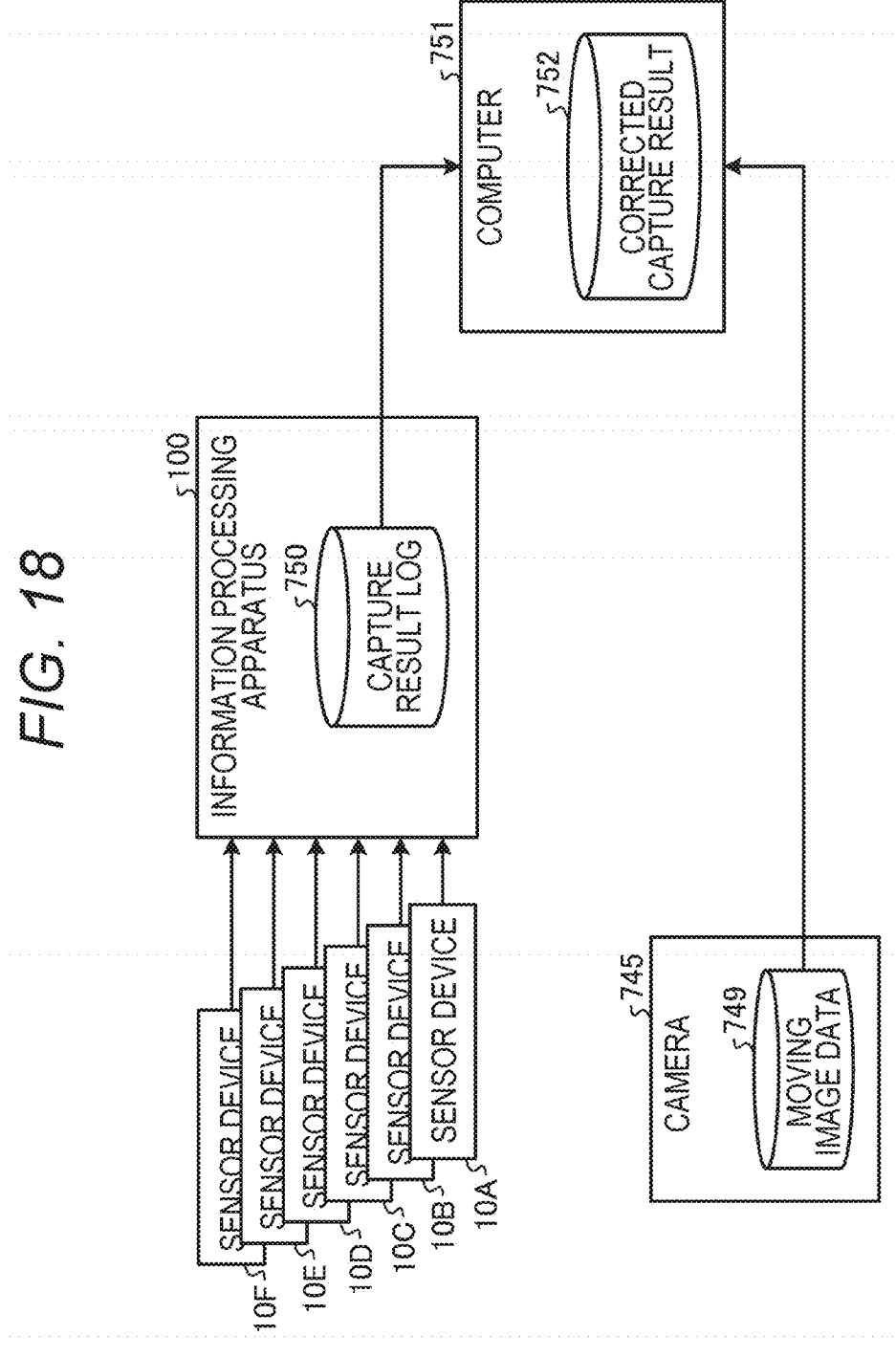
FIG. 18 is a diagram illustrating a configuration example of a system that executes information processing according to the second modification.

FIG. 18 illustrates a configuration example of a system in a case of executing information processing according to the second modification. FIG. 18 is a diagram illustrating a configuration example of a system that executes the information processing according to the second modification.

As illustrated in FIG. 18, the post-process processing may be executed by cooperation of the information processing apparatus 100 and a computer 751. The information processing apparatus 100 acquires the sensor data from the sensor devices 10A to 10F, and stores the sensor data in the storage unit as a capture result log 750.

Furthermore, the camera 745 holds moving image data 749 obtained by imaging the user 14 and the background according to the operation by the operator.

The computer 751 generates and holds a corrected capture result 752 on the basis of the capture result log 750 acquired from the information processing apparatus 100 and the moving image data 749 acquired from the camera 745. The corrected capture result 752 may be paraphrased as corrected skeleton data generated by the post-process processing. Furthermore, the computer 751 may generate avatar distribution video or the like by synthesizing the avatar video in which the corrected capture result 752 is applied to the avatar 747 and the background data of the moving image data 749.

In this manner, by generating the corrected skeleton data reflecting the movement of the user 14 and applying the corrected skeleton data to the avatar later, the information processing apparatus 100 can provide the avatar video as augmented reality (AR) content in which only the avatar is superimposed on a real background, for example.

Note that, in the example of FIG. 18, the calculation processing is performed in the post-process processing, and thus the computer 751 is illustrated assuming a server device or the like that is assumed to have higher calculation capability than the information processing apparatus 100. However, such processing may be executed only by the information processing apparatus 100.

(1-5-3. Use Example of Additional Information Obtained from Camera)

Figure 19:
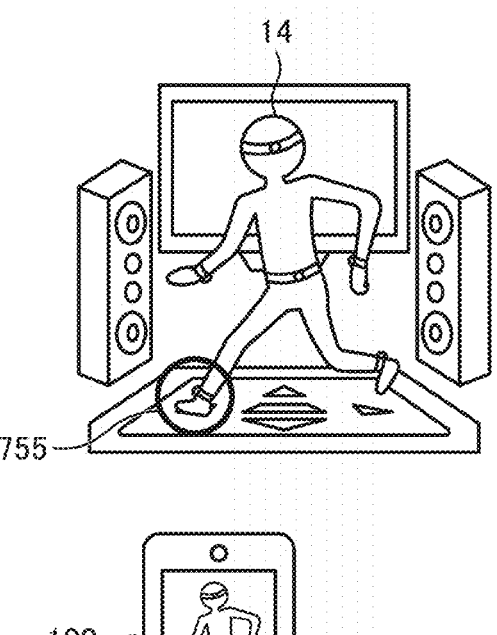
FIG. 19 is a diagram illustrating an outline of information processing according to a third modification.

Next, a third modification will be described with reference to FIG. 19. FIG. 19 is a diagram illustrating an outline of information processing according to the third modification.

In the example illustrated in FIG. 19, information processing of reflecting grounding information and the like in the posture information, which is difficult only with the inertial data, on the basis of a feature of the information processing according to the embodiment of calculating the posture information on the basis of the information obtained by the camera, will be described.

In the example illustrated in FIG. 19, the information processing apparatus 100 images the user 14 using the camera 140 to acquire not only the skeleton information but also the grounding information of a foot end position 755 of the user 14, for example. Specifically, the information processing apparatus 100 performs processing of detecting whether or not the foot end position 755 is grounded from the image information acquired by the camera 140.

In a case of determining that the foot end position 755 is grounded, the information processing apparatus 100 reflects information of the grounding in the posture information to be calculated. Normally, in a case where the inertial data is used, since a result estimated from the inertial data obtained from the ankle or the like is used for grounding of the end position of the user 14, there is a concern that accuracy of the grounding detection may be lowered. However, in the case of the data obtained by imaging the user 14, it is possible to more accurately detect the grounding of the foot end position 755 than the estimation by the inertial data.

As described above, in a case where it is detected that at least a part of the user 14 has come in contact with an arbitrary target object such as the ground on the basis of the image information, the display control unit 168 according to the information processing apparatus 100 performs the display control of the avatar in accordance with the detection. Therefore, the information processing apparatus 100 can prevent a defect in the display processing due to insufficient accuracy of the grounding detection, such as a foot of the avatar getting stuck in the ground or floating from the ground, which is likely to occur when displaying the avatar reflecting the movement of the user 14. Note that various known techniques may be applied to processing of recalculating the posture information associated with grounding, and the like.

Furthermore, the information processing apparatus 100 may detect grounding (contact) of portions other than the foot and generate the corrected skeleton data with higher accuracy.

For example, the information processing apparatus 100 aligns and sets the position of an object in a virtual space and the position of an object in a real space on the basis of the video by the camera. Then, when detecting that the user 14 has come in contact with the object in the real space, the information processing apparatus 100 performs display control such that the avatar touches the associated object in the virtual space. Specifically, the information processing apparatus 100 aligns and sets the position of a desk in the virtual space with a desk in the real space included in the image information imaged by the camera 140, and displays the desk in the virtual space together with the avatar. Then, in a case of detecting that the user 14 has touched the real desk, the information processing apparatus 100 can perform display control such that the avatar comes in contact with the desk in the video or perform effect display based on the contact by providing the posture information indicating that the avatar has come in contact with the desk displayed in the virtual space. Note that, when performing AR display, the information processing apparatus 100 may perform the effect display based on the contact on the AR display when detecting that the user has come in contact with the real object. Note that the effect display based on the contact may be performed at or near a contact position, or may be performed on the entire screen.

Furthermore, as an example of use of additional information obtained from the camera 140, the information processing apparatus 100 can perform tracking of fingers or the face (expression) of the user 14 from the camera image, and perform avatar display control in combination with the inertial skeleton data 20. In this case, the information processing apparatus 100 uses the image information from the camera 140 for finger tracking and face tracking that are difficult to obtain with the inertial motion capture system.

As described above, the display control unit 168 according to the information processing apparatus 100 may detect expression information of the moving body (for example, detect the face of the user 14) on the basis of the image information imaged by the camera 140, the camera 745, or the like, and perform the avatar display control on the basis of a detection result. Furthermore, the display control unit 168 may detect finger information of the moving body (for example, detect an end such as the hand or fingers of the user 14) on the basis of the image information imaged by the camera 140, the camera 745, or the like, and perform avatar display control on the basis of a detection result. Note that the above-described tracking may be executed on the basis of not only the detection result by the camera 140 but also information acquired from another device. For example, the information processing apparatus 100 can track the fingers of the user 14 by capturing the movement (gesture) of the moving body in time series on the basis of information detected from the inertial sensor attached to the end (fingertip) of the moving body. Furthermore, the information processing apparatus 100 can track the expression of the user 14 by capturing the movement (expression) of the face of the moving body in time series using, for example, a sensor that detects the movement of muscles of expression of the moving body. That is, the above-described tracking processing is not limited to a method of imaging the moving body with the camera. Moreover, the information processing apparatus 100 may perform the tracking by combining a plurality of devices by using the information acquired by the sensor device as described above for the tracking and using the image information acquired by the camera as auxiliary information for the tracking.

That is, the information processing apparatus 100 combines the inertial skeleton data generated on the basis of the information acquired from the inertial sensor worn by the user 14 and the posture information of the face or the hand generated on the basis of the image information of the user 14 acquired from the camera to generate the posture information to be used for the avatar display.

Therefore, the information processing apparatus 100 can perform avatar expression more accurately reflecting the real movement of the user 14.

Note that the information processing apparatus 100 may use the camera image for either or both of finger and face (expression) tracking. Furthermore, the information processing apparatus 100 may perform the avatar display control by using the camera image for correction of the inertial skeleton data and further using the camera image for tracking the face and the fingers in combination.

(1-5-4. Capture Example of Plurality of Moving Bodies)

Figure 20:
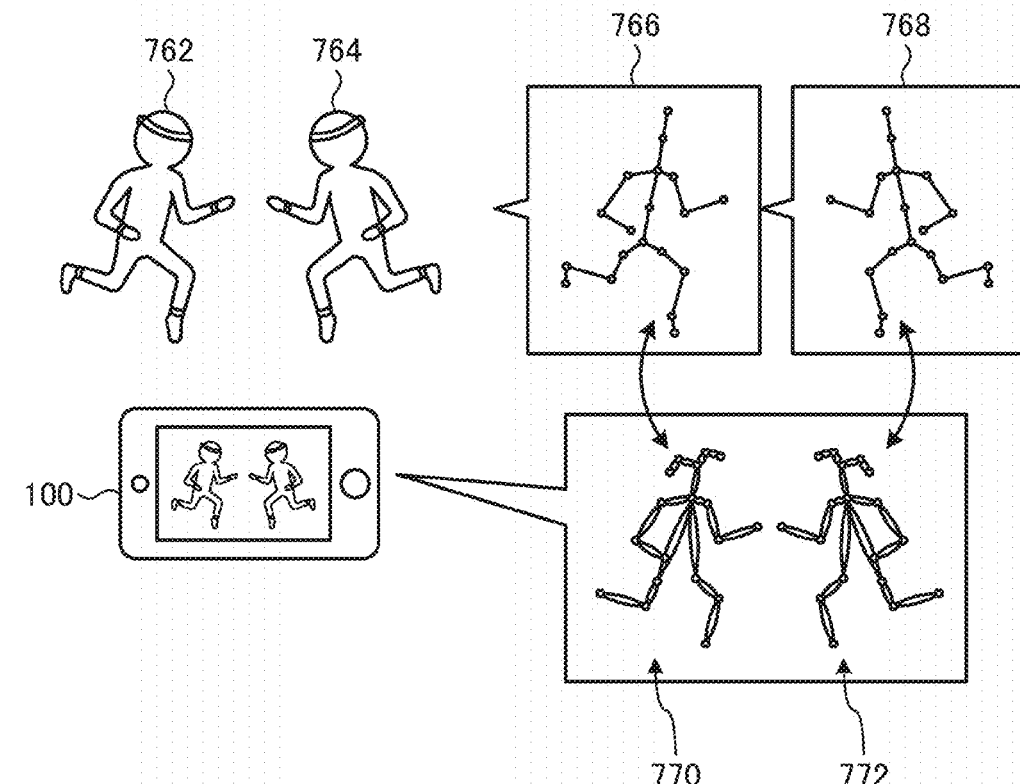
FIG. 20 is a diagram illustrating an outline of information processing according to a fourth modification.

Next, a third modification will be described with reference to FIG. 20. FIG. 20 is a diagram illustrating an outline of information processing according to the fourth modification.

In the example illustrated in FIG. 20, processing in which motion capture according to the embodiment is executed for a plurality of moving bodies will be described. That is, the information processing apparatus 100 can apply the motion capture according to the embodiment not only to one user (moving body) but also to a plurality of users.

In the example illustrated in FIG. 20, the information processing apparatus 100 acquires the inertial data from the sensor devices respectively worn by a plurality of users such as a user 762 and a user 764. Then, the information processing apparatus 100 generates inertial skeleton data 766 and inertial skeleton data 768 on the basis of pieces of the inertial data corresponding to the respective users.

Furthermore, the information processing apparatus 100 acquires the image information by imaging the plurality of users such as the user 762 and the user 764 with a camera included in its own apparatus. The information processing apparatus 100 generates optical skeleton data 770 and optical skeleton data 772 corresponding to the user 762 and the user 764 on the basis of the image information.

At this time, the information processing apparatus 100 determines each degree of similarity between the first posture information (inertial skeleton data) of each of the plurality of different moving bodies obtained on the basis of the inertial information and the second posture information (optical skeleton data) of each of the plurality of moving bodies obtained from the image information obtained by imaging the plurality of moving bodies. Specifically, to determine to which user the optical skeleton data included in the image information corresponds, the information processing apparatus 100 determines each degree of similarity between the inertial skeleton data and the optical skeleton data, and specifies which inertial skeleton data and optical skeleton data correspond to each other. Then, the information processing apparatus 100 executes the information processing according to the embodiment on the basis of a specified result, and generates the corrected skeleton data of each user. Note that the above-described determination of the degree of similarity can be performed by using a known technique such as a method of comparing various types of information such as the shape and scale of the skeleton and the orientation of the body to calculate the degree of similarity.

In this manner, the information processing apparatus 100 determines the degree of similarity between the inertial skeleton data and the optical skeleton data, and specifies the user with which each piece of data is associated on the basis of the degree of similarity, thereby executing the information processing according to the embodiment without any trouble even in a case where a plurality of users enters the angle of view.

(1-5-5. Use of Self-Position Estimation of Camera)

Next, a fifth modification will be described with reference to FIG. 21. FIG. 21 is a flowchart illustrating a procedure of information processing according to the fifth modification.

The fifth modification illustrates processing executed by the information processing apparatus 100 in a case where it is assumed that the camera is not a fixed camera and the camera moves after calibration.

For example, when the user tries to images an object, using the camera 140 included in the information processing apparatus 100 while moving the information processing apparatus 100, there is a possibility that the parameters at the time of calibration cannot be used and accurate corrected skeleton data cannot be generated. As described above, in a case where the camera is not a fixed camera, the information processing apparatus 100 updates the calibration parameters in accordance with the movement of the camera on the basis of the self-position estimation processing (simultaneous localization and mapping (SLAM)) or the like) executed by the camera. Specifically, the information processing apparatus 100 updates the scale factors from a movement amount in the depth direction or a posture change amount due to rotation (pitch or yaw) estimated by the camera. Furthermore, the information processing apparatus 100 updates the coordinate transformation matrix from vertical and horizontal movement amounts and a posture change amount of roll. As a result, the information processing apparatus 100 can implement the information processing according to the embodiment without any trouble even in a case where imaging is performed by the camera that is not a fixed camera.

Such processing will be described along a flow with reference to FIG. 21. As illustrated in FIG. 21, the information processing apparatus 100 first holds the parameters acquired at the time of calibration (step S61).

Thereafter, the information processing apparatus 100 determines whether or not the camera has moved (step S62). For example, in a case of performing imaging by the camera included in its own apparatus, the information processing apparatus 100 determines whether or not the camera has moved on the basis of information (acceleration sensor, position information, or the like) indicating that its own apparatus has moved. Furthermore, in a case of using an external camera, the information processing apparatus 100 receives information (acceleration sensor, position information, or the like) indicating that the external camera has moved by communication from the external camera, and determines whether or not the camera has moved on the basis of the received information.

In a case where the camera does not move (step S62; No), update of the parameters at the time of calibration is not necessary. Therefore, the information processing apparatus 100 applies the parameters at the time of calibration as they are (step S63).

On the other hand, in a case where the camera has moved (step S62; Yes), after acquiring the frame (image information) imaged by the camera (step S64), the information processing apparatus 100 estimates a self-position and the posture of the camera (step S65). For example, the information processing apparatus 100 receives various data from the camera on the basis of the SLAM described above, and estimates the self-position and posture of the camera on the basis of the received information.

Then, the information processing apparatus 100 derives the movement amount in the depth direction and the posture change amounts of pitch and yaw in the camera from the self-position and the posture information of the camera, and updates the scale factors (step S66).

Furthermore, the information processing apparatus 100 derives the vertical and horizontal movement amounts and the posture change amount of the roll in the camera, and updates the coordinate transformation matrix (step S67).

Then, the information processing apparatus 100 applies the parameters updated in steps S66 and S67 (step S68). Thereafter, the information processing apparatus 100 determines whether or not the capture has ended (step S69). In a case where the capture has not ended (step S69; No), the information processing apparatus 100 performs the information processing according to the embodiment by applying the updated parameters to the next frame, and further repeatedly updates the camera parameters on the basis of the self-position information of the camera or the like. On the other hand, when the capture ends (step S69; Yes), the information processing apparatus 100 also terminates the parameter update processing.

In this manner, the calculation unit 166 according to the information processing apparatus 100 may recalculate the parameters in the calibration on the basis of the position and the posture information of the camera estimated on the basis of the image information, and calculate the corrected skeleton data on the basis of the result of the recalculation. Note that, in the above example, an example in which the information processing apparatus 100 estimates the self-position and the like of the camera on the basis of the SLAM has been described, but the self-position estimation of the camera is not limited to such a technique. For example, the information processing apparatus 100 may capture the position information of the camera by the user giving a marker to the camera and measuring the marker with an external camera.

(1-5-6. System Configuration Example in Case of Using External Device)

Next, a sixth modification will be described with reference to FIG. 22. FIG. 22 is a diagram illustrating a configuration example of a system that executes information processing according to the sixth modification.

The sixth modification illustrates an example in which the information processing apparatus 100 uses a globe 302 or an external camera 304 as a device for capturing the motion of the user. The globe 302 is, for example, a sensor device having a function of recognizing the posture of wearer's fingers.

Furthermore, in the example of FIG. 22, the information processing apparatus 100 includes a background data acquisition unit 300. For example, the background data acquisition unit 300 acquires, from the external camera 304, the image information to be used in the background when the avatar is displayed.

In other words, in a case where the globe 302 is connected to the information processing apparatus 100, the information processing apparatus 100 may generate the skeleton data on the basis of the posture information of the fingers acquired from the globe 302, and perform the avatar display control. Furthermore, the information processing apparatus 100 may perform the avatar display control using the image information acquired from the external camera 304 as the background of the avatar.

As described above, the information processing apparatus 100 can execute the information processing according to the embodiment using, not limited to the sensor device 10, various devices capable of acquiring the posture information.

(1-5-7. Modification of Information Processing System)

FIGS. 23 to 28 are diagrams illustrating a seventh modification. The seventh modification illustrates a modification of the information processing system 1 illustrated in FIG. 2.

For example, the example of FIG. 3 illustrates an example in which the corrected skeleton data generated by the information processing apparatus 100 is applied to the avatar display control, and the distribution server 30 distributes the avatar to the viewing user. However, the processing of applying (retargeting) the corrected skeleton data to the avatar and the processing of distributing the retargeted avatar may be executed by various entities. That is, the seventh modification illustrates types of a process until the capture data is used by the user after the information processing apparatus 100 executes the motion capture (so-called post (subsequent) processing such as distribution to the user). More specifically, modes of the seventh modification can be exemplified as use cases 1 to 6 illustrated in FIGS. 23 to 28. Hereinafter, the use cases 1 to 6 will be described in order.

FIG. 23 is a diagram illustrating the use case 1 of the seventh modification. As illustrated in FIG. 23, in the use case 1, the information processing apparatus 100 includes a motion capture unit 780 and a distribution application 782. The distribution application 782 is software that executes distribution processing in the use case 1. That is, the use case 1 illustrates an example in which the information processing apparatus 100 plays a role of utilization and distribution of data obtained by the motion capture in its own apparatus.

The motion capture unit 780 corresponds to the control unit 160 in the above-described embodiment. That is, the motion capture unit 780 generates the corrected skeleton data using the inertial skeleton data generated on the basis of the acquired sensor data and the optical skeleton data generated on the basis of the image information of the camera.

The distribution application 782 is responsible for processing of distributing the avatar image generated on the basis of the motion capture data (corrected skeleton data) acquired by the motion capture unit 780. As illustrated in FIG. 23, the distribution application 782 includes an acquisition unit 791, a retargeting unit 784, and a distribution unit 786.

The acquisition unit 791 acquires, from the motion capture unit 780, motion capture data that is data for imparting movement to the avatar. The motion capture data may be the corrected skeleton data itself or posture information based on various existing formats generated on the basis of the corrected skeleton data. The retargeting unit 784 reapplies (retargets) the motion capture data acquired by the acquisition unit 791 from the user 14 of which the movement has been captured to another character or the like. For example, the retargeting unit 784 applies the motion capture data obtained by capturing the movement of the user 14 to the avatar on the virtual content such as VR.

The distribution unit 786 distributes the avatar image generated by the retargeting unit 784 via the network 12 or the distribution server 30. Note that the information processing apparatus 100 may directly distribute the avatar image to the user 15 without the distribution server 30.

As described above, the configuration of the use case 1 includes the distribution application 782 in which the information processing apparatus 100 executes the retargeting processing and the distribution processing. That is, in the use case 1, the information processing apparatus 100 further includes the retargeting unit 784 that applies the posture information calculated by the calculation unit 166 to the virtual content (avatar or the like), and the distribution unit 786 that distributes the virtual content to which the posture information is applied by the retargeting unit 784 to the user.

In the case of the use case 1, a distributor can execute the motion capture and execute the subsequent avatar image generation and distribution by using only the information processing apparatus 100. That is, according to the configuration of the use case 1, the distributor can distribute, to the user, the avatar on which the highly accurate motion capture has been performed with a simple configuration such as one smartphone.

Next, the use case 2 of the seventh modification will be described. FIG. 24 is a diagram illustrating the use case 2 of the seventh modification. The use case 2 illustrates an example in which a distribution application 782A is designed by a developer 16, and the information processing apparatus 100 incorporates a distribution application 782A designed by the developer 16 into its own apparatus.

The distribution application 782A further includes a conversion unit 792 as compared with the example of FIG. 23. The conversion unit 792 is, for example, a processing unit incorporated in the distribution application 782A as a plug-in for using the motion capture data generated by the motion capture unit 780 in the distribution application 782A. That is, the use case 2 illustrates an example in which the information processing apparatus 100 provides the developer 16 with a function for using the motion capture data as a plug-in, and performs distribution using the distribution application 782A in which such a function is incorporated.

The conversion unit 792 acquires various data from the acquisition unit 791, and converts the data into a format that can be handled by the distribution application 782A. For example, the conversion unit 792 receives the corrected skeleton data from the acquisition unit 791, and converts the corrected skeleton data into a form that can be retargeted by the retargeting unit 784. The retargeting unit 784 retargets the corrected skeleton data converted by the conversion unit 792 to the avatar or the like. The distribution unit 786 distributes the retargeted avatar to the user 15.

As described above, in the use case 2, the information processing apparatus 100 includes the conversion unit 792 that converts the corrected skeleton data into a format readable by the display control unit 168 so that the corrected skeleton data can be retargeted to the avatar and display-controlled.

In the case of the use case 2, the distributor who uses the information processing apparatus 100 does not need to develop the distribution application 782A in its own apparatus, and enables the avatar distribution in its own apparatus by providing the function as a plug-in to the distribution application 782A developed by the external developer 16. That is, even in a case where the software used for distribution is externally developed, the information processing apparatus 100 can apply the information processing according to the embodiment and perform the avatar distribution by its own apparatus.

Next, the use case 3 of the seventh modification will be described. FIG. 25 is a diagram illustrating the use case 3 of the seventh modification. The use case 3 illustrates an example in which the information processing apparatus 100 does not directly distribute the avatar but provides the avatar to a data use apparatus 800 that is another apparatus using the motion capture data generated by the information processing apparatus 100, and the data use apparatus 800 distributes the avatar.

The data use apparatus 800 is, for example, a server device operated by a business operator different from the information processing apparatus 100 or a cloud server arranged on a cloud. The data use apparatus 800 includes a distribution application 810 for acquiring the corrected skeleton data via the network 12, retargeting the acquired data to the avatar, and distributing the retargeted avatar. That is, the use case 3 illustrates an example in which the functions of the retargeting unit 784 and the distribution unit 786 executed by the information processing apparatus 100 in the use case 1 are executed on software (distribution application 810) included in the data use apparatus 800. Note that an acquisition unit 812 related to the distribution application 810 executes processing similar to that of the acquisition unit 791 illustrated in FIG. 23. A retargeting unit 814 related to the distribution application 810 executes processing similar to that of the retargeting unit 784 illustrated in FIG. 23. A distribution unit 816 related to the distribution application 810 executes processing similar to that of the distribution unit 786 illustrated in FIG. 23.

As described above, in the use case 3, the information processing apparatus 100 transmits the corrected skeleton data generated by the motion capture unit 780 to the data use apparatus 800 via the communication unit 130. The data use apparatus 800 includes the retargeting unit 784 that applies the posture information calculated by the calculation unit 166 according to the information processing apparatus 100 to the virtual content (avatar or the like), and the distribution unit 786 that distributes the virtual content to which the posture information has been applied by the retargeting unit 784 to the user.

In other words, the communication unit 130 according to the information processing apparatus 100 provides the corrected skeleton data to another apparatus (the data use apparatus 800) that performs the avatar display control coupled to the movement of the user 14 on the basis of the corrected skeleton data. According to the use case 3, some of the functions of the information processing apparatus 100 can be executed by the data use apparatus 800. Therefore, in the system configuration of the use case 3, even in a case where the information processing apparatus 100 is an apparatus having a low processing capability such as a smartphone, the processing load can be shared with the data use apparatus 800, so that the information processing according to the embodiment can be smoothly executed.

Next, the use case 4 of the seventh modification will be described. FIG. 26 is a diagram illustrating the use case 4 of the seventh modification. The use case 4 illustrates an example in which the external developer 16 provides a communication application 794 for allowing the information processing apparatus 100 to transmit the corrected skeleton data to the data use apparatus 800 and the distribution application 810 used by the data use apparatus 800 for distribution.

In the case of the use case 4, similarly to the use case 2, the information processing apparatus 100 provides the conversion unit 792 as a plug-in executed by the communication application 794. In the processing in the communication application 794, the conversion unit 792 acquires the corrected skeleton data from the motion capture unit 780, and converts the acquired data into a format that can be handled by the communication application 794. Furthermore, the communication unit 130 transmits the corrected skeleton data converted by the conversion unit 792 to the data use apparatus 800.

As a result, the information processing apparatus 100 can allow use of the corrected skeleton data generated by its own apparatus without any trouble even if the communication application 794 and the distribution application 810 are software provided by the developer 16.

Next, the use case 5 of the seventh modification will be described. FIG. 27 is a diagram illustrating the use case 5 of the seventh modification. The use case 5 illustrates a situation in which the data use apparatus 800 is operated by the external developer 16.

In this case, the information processing apparatus 100 provides a plug-in to be incorporated in a conversion application 820 developed by the developer 16. For example, in a case where the conversion application 820 performs processing, the plug-in executes processing of transmitting a request for acquiring the corrected skeleton data to the information processing apparatus 100 and processing of acquiring the corrected skeleton data from the information processing apparatus 100. Specifically, the communication unit 130 according to the information processing apparatus 100 transmits the corrected skeleton data to the conversion application 820 in the case of receiving the request for acquiring the corrected skeleton data from the conversion application 820. An acquisition unit 822 related to the conversion application 820 acquires the corrected skeleton data transmitted by the communication unit 130. A conversion unit 824 converts the acquired corrected skeleton data into a format that can be handled by a retargeting unit 826. The retargeting unit 826 applies the converted corrected skeleton data to the avatar. Furthermore, a distribution unit 828 distributes the retargeted avatar image to the distribution server 30 and the user 15.

According to the use case 5, since the conversion application 820 is responsible for the processing of applying the corrected skeleton data to the avatar, the information processing apparatus 100 can provide the avatar image generated with high accuracy to the user 15 only by providing the corrected skeleton data to the external apparatus using a plug-in or the like without performing retargeting or distribution by its own apparatus.

Next, the use case 6 of the seventh modification will be described. FIG. 28 is a diagram illustrating the use case 6 of the seventh modification. The use case 6 illustrates an example in which a conversion application 830 related to the data use apparatus 800 is responsible only for data conversion, and a retargeting unit 836 and a distribution unit 838 are configured as different types of software. Note that the use case 6 also indicates a situation where the data use apparatus 800 is operated by the external developer 16.

In this case, the information processing apparatus 100 provides a plug-in to be incorporated in a conversion application 830 developed by the developer 16, similarly to the use case 5. An acquisition unit 832 related to the conversion application 830 acquires the corrected skeleton data transmitted by the communication unit 130. A conversion unit 834 converts the acquired corrected skeleton data into a format that can be handled by the retargeting unit 836. The retargeting unit 784 applies the converted corrected skeleton data to the avatar. Furthermore, the distribution unit 838 distributes the retargeted avatar image to the distribution server 30 and the user 15.

As described above, the information processing apparatus 100 can provide the avatar image generated with high accuracy to the user 15 only by providing the corrected skeleton data to the external apparatus from its own device using the plug-in or the like regardless of the software configuration of the data use apparatus 800.

Although the configuration examples of the plurality of systems have been described above as the seventh modification, these systems are applicable to all of the first to sixth embodiments.

2. Other Embodiments

The processing according to each of the above-described embodiments may be performed in various different forms other than the above-described embodiments.

Furthermore, among the respective processes described in the above-described embodiments, all or a part of the processes described as being performed automatically can be performed manually, or all or a part of the processes described as being performed manually can be performed automatically by a known method. In addition, information including the processing procedures, the specific names, and the various data and parameters illustrated in the document and the drawings described above can be arbitrarily changed unless otherwise specified. For example, the various pieces of information illustrated in each of the drawings are not limited to the illustrated information.

Furthermore, each component of each device illustrated in the drawings is functionally conceptual, and is not necessarily physically configured as illustrated. That is, the specific form of distribution or integration of each of the devices is not limited to the one illustrated in the drawings, and all or a part of the device can be functionally or physically distributed or integrated in any units according to various loads, usage conditions, or the like.

Furthermore, the embodiments and modification examples as have been described above can be appropriately combined within a range in which the processing contents do not contradict each other.

Furthermore, the effects described in the present description are merely examples and are not limited, and other effects may be provided.

3. Effects of Information Processing Apparatus According to the Present Disclosure As described above, the information processing apparatus (the information processing apparatus 100 in the embodiment) according to the present disclosure includes a first acquisition unit (the inertial data acquisition unit 162 in the embodiment), a second acquisition unit (the optical data acquisition unit 163 in the embodiment), and a calculation unit (the calculation unit 166 in the embodiment). The first acquisition unit acquires inertial information associated with a movement of a moving body (for example, the user 14) from an inertial sensor attached to the moving body. The second acquisition unit acquires first image information obtained by imaging the moving body from a first camera (for example, the camera 140). The calculation unit calculates third posture information (for example, the corrected skeleton data 24) on the basis of first posture information (for example, inertial skeleton data 20) of the moving body obtained on the basis of the inertial information acquired by the first acquisition unit and second posture information (for example, the optical skeleton data 22) of the moving body obtained on the basis of the first image information acquired by the second acquisition unit.

Note that the calculation unit calculates the third posture information by correcting the first posture information on the basis of the second posture information.

Furthermore, the calculation unit estimates the degree of reliability regarding the second posture information, and performs the correction according to the degree of reliability. For example, the calculation unit estimates the degree of reliability according to reliability of environment information when the first camera images the moving body or of the second posture information of the moving body obtained from the first image information.

As described above, the information processing apparatus according to the present disclosure improves the accuracy of motion capture by calculating the corrected skeleton data obtained by correcting the inertial skeleton data obtained by inertial motion capture with the optical skeleton data obtained by camera imaging. For example, data by the inertial motion capture has a disadvantage of an increase in an error with time. However, according to the information processing apparatus, such an error is corrected on the basis of data by a camera, it is possible to continue execution of motion capture while maintaining high accuracy for a long time.

Furthermore, the information processing apparatus further includes a display control unit (the display control unit 168 in the embodiment) configured to perform display control of an object coupled to the movement of the moving body on the basis of the third posture information.

For example, the display control unit displays the object (for example, an avatar displayed in virtual content, or the like) superimposed on the first image information.

As described above, since the information processing apparatus displays the object on the basis of the corrected skeleton data, it is possible to perform display control in which the movement of the moving body is reflected with high accuracy.

Furthermore, the second acquisition unit acquires second image information including a background image from a second camera different from the first camera.

Then, the display control unit superimposes and displays the object on the background image included in the second image information.

Furthermore, in a case of detecting contact of at least a part of the moving body with a target object on the basis of the first image information, the display control unit performs display control of the object in response to the detection.

As described above, since the information processing apparatus acquires the image information from the camera and performs each processing, the information processing apparatus can perform various avatar displays and the like using the background image and the like that cannot be acquired only from the inertial data.

Furthermore, the calculation unit performs preprocessing (calibration) of calculating a predetermined parameter such that size and joint information of the moving body obtained from the inertial information matches size and joint information of the moving body obtained from the first image information, and calculates the third posture information on the basis of the preprocessing.

Moreover, the calculation unit may recalculate the predetermined parameter in the preprocessing on the basis of position and posture information of the first camera estimated on the basis of the first image information, and calculate the third posture information on the basis of a result of the recalculation.

As described above, the information processing apparatus can accurately perform the correction processing using the inertial data and the optical data (image) by performing the preprocessing of matching scales and the like of the mutual data.

Furthermore, the display control unit detects expression information of the moving body on the basis of the first image information or the second image information, and performs display control of the object on the basis of a detection result.

Furthermore, the display control unit may detect finger information of the moving body on the basis of the first image information or the second image information, and perform display control of the object on the basis of a detection result.

As described above, the information processing apparatus can track an expression (face) or fingers of the moving body by using the camera, and reflect a tracking result in the motion capture, and thus can perform posture information calculation and avatar display that accurately reflect the movement of the moving body.

Furthermore, the first acquisition unit acquires a plurality of pieces of the inertial information associated with respective movements of the moving body from the inertial sensors attached to a plurality of the moving bodies that is different. The second acquisition unit acquires third image information (the captured image illustrated in FIG. 20 in the embodiment) obtained by simultaneously imaging the plurality of different moving bodies. The calculation unit determines the degree of similarity between the first posture information (the inertial skeleton data 766 and the inertial skeleton data 768 illustrated in FIG. 20 in the embodiment) of each of the plurality of different moving bodies obtained on the basis of the inertial information and the second posture information (the optical skeleton data 770 and the optical skeleton data 772 illustrated in FIG. 20 in the embodiment) of each of the plurality of different moving bodies obtained from the third image information. Moreover, the calculation unit specifies the second posture information corresponding to the first posture information of the plurality of different moving bodies on the basis of the determined degree of similarity, and then calculates the third posture information of each of the plurality of different moving bodies.

As described above, even in a case where a plurality of moving bodies is captured at the same time, the information processing apparatus can correct the skeleton data of a plurality of users without any trouble by determining the degree of similarity between each piece of the inertial skeleton data and each piece of the optical skeleton data.

Furthermore, the information processing apparatus may further include a communication unit (the communication unit 130 in the embodiment) that provides the third posture information to another apparatus (the data use apparatus 800 or the like in the embodiment) that performs display control of an object coupled to the movement of the moving body on the basis of the third posture information.

As described above, the information processing apparatus can share a data processing load or cause the another apparatus to perform only distribution processing by providing the corrected skeleton data to the another apparatus. Therefore, the information processing apparatus can appropriately use the corrected skeleton data having high accuracy even in a case where the its own apparatus does not have high calculation capability or cannot perform the distribution processing.

4. Hardware Configuration

An information apparatus such as the information processing apparatus 100 or the distribution server 30 according to each of the above-described embodiments is implemented by, for example, a computer 1000 having a configuration as illustrated in FIG. 29. Description will be given below taking the information processing apparatus 100 according to an embodiment as an example. FIG. 29 is a hardware configuration diagram illustrating an example of the computer 1000 that implements a function of the information processing apparatus 100. The computer 1000 has a CPU 1100, a RAM 1200, a read only memory (ROM) 1300, a hard disk drive (HDD) 1400, a communication interface 1500, and an input-output interface 1600. Each unit of the computer 1000 is connected by a bus 1050.

The CPU 1100 operates on the basis of a program stored in the ROM 1300 or the HDD 1400, and controls each unit. For example, the CPU 1100 develops the program stored in the ROM 1300 or the HDD 1400 in the RAM 1200, and executes processing corresponding to various programs.

The ROM 1300 stores a boot program such as a basic input output system (BIOS) executed by the CPU 1100 when the computer 1000 is activated, a program depending on hardware of the computer 1000, and the like.

The HDD 1400 is a computer-readable recording medium that non-transiently records the program executed by the CPU 1100, data used by the program and the like. Specifically, the HDD 1400 is a recording medium that records a display program according to the present disclosure, which is an example of program data 1450.

The communication interface 1500 is an interface for the computer 1000 to connect to an external network 1550 (for example, the Internet). For example, via the communication interface 1500, the CPU 1100 receives data from another apparatus or transmits data generated by the CPU 1100 to another apparatus.

The input-output interface 1600 is an interface for connecting the input-output device 1650 and the computer 1000. For example, the CPU 1100 receives data from an input device such as a keyboard and a mouse via the input-output interface 1600. Furthermore, via the input-output interface 1600, the CPU 1100 transmits data to an output device such as a display, a speaker, or a printer. Furthermore, the input-output interface 1600 may function as a media interface for reading a program or the like recorded on a predetermined recording medium (medium). The medium is, for example, an optical recording medium such as a digital versatile disc (DVD) and a phase change rewritable disk (PD), a magneto-optical recording medium such as a magneto-optical disk (MO), a tape medium, a magnetic recording medium, a semiconductor memory or the like.

For example, in a case where the computer 1000 functions as the information processing apparatus 100 according to the embodiment, the CPU 1100 of the computer 1000 implements a function of the control unit 160 or the like, by executing a display program loaded into the RAM 1200. Furthermore, the HDD 1400 stores the information processing program according to the present disclosure or data in the storage unit 150. Note that, although the CPU 1100 reads the program data 1450 from the HDD 1400 and executes the program data 1450, as another example, these programs may be acquired from another device via the external network 1550.

Note that the present technology may also have the following configuration.

(1)

An information processing apparatus including:

a first acquisition unit configured to acquire, from an inertial sensor attached to a moving body, inertial information associated with a movement of the moving body;

a second acquisition unit configured to acquire first image information obtained by imaging the moving body from a first camera; and a calculation unit configured to calculate third posture information on the basis of first posture information of the moving body obtained on the basis of the inertial information acquired by the first acquisition unit and second posture information of the moving body obtained on the basis of the first image information acquired by the second acquisition unit.

(2)

The information processing apparatus according to (1) above, in which the calculation unit calculates the third posture information by correcting the first posture information on the basis of the second posture information.

(3)

The information processing apparatus according to (2) above, in which the calculation unit estimates a degree of reliability regarding the second posture information, and performs the correction according to the degree of reliability.

(4)

The information processing apparatus according to (3) above, in which the calculation unit estimates the degree of reliability according to reliability of environment information when the first camera images the moving body or of the second posture information of the moving body obtained from the first image information.

(5)

The information processing apparatus according to any one of (1) to (4) above, further including:

a display control unit configured to perform display control of an object coupled to the movement of the moving body on the basis of the third posture information.

(6)

The information processing apparatus according to (5) above, in which the display control unit displays the object by superimposing the object on the first image information.

(7)

The information processing apparatus according to (5) or (6) above, in which the second acquisition unit acquires second image information including a background image from a second camera different from the first camera.

(8)

The information processing apparatus according to (7) above, in which the display control unit displays the object by superimposing the object on the background image included in the second image information.

(9)

The information processing apparatus according to any one of (5) to (8) above, in which, in a case of detecting contact of at least a part of the moving body with a target object on the basis of the first image information, the display control unit performs display control of the object in response to the detection.

(10)

The information processing apparatus according to any one of (1) to (9) above, in which the calculation unit performs preprocessing of calculating a predetermined parameter such that size and joint information of the moving body obtained from the inertial information matches size and joint information of the moving body obtained from the first image information, and calculates the third posture information on the basis of the preprocessing.

(11)

The information processing apparatus according to (10) above, in which the calculation unit recalculates the predetermined parameter in the preprocessing on the basis of position and posture information of the first camera estimated on the basis of the first image information, and calculates the third posture information on the basis of a result of the recalculation.

(12)

The information processing apparatus according to any one of (7) to (9) above, in which the display control unit detects expression information of the moving body on the basis of the first image information or the second image information, and performs display control of the object on a basis of a detection result.

37

38

(13)

The information processing apparatus according to any one of (7) to (9) or (12) above, in which the display control unit detects finger information of the moving body on the basis of the first image information or the second image information, and performs display control of the object on a basis of a detection result.

(14)

The information processing apparatus according to any one of (1) to (13) above, in which the first acquisition unit acquires, from the inertial sensors attached to a plurality of the moving bodies that is different, a plurality of pieces of the inertial information associated with the movements of the respective moving bodies, the second acquisition unit acquires third image information obtained by simultaneously imaging the plurality of different moving bodies, and the calculation unit determines a degree of similarity between the first posture information of each of the plurality of different moving bodies obtained on the basis of the inertial information and the second posture information of each of the plurality of different moving bodies obtained from the third image information, specifies the second posture information corresponding to the first posture information of the plurality of different moving bodies on the basis of the determined degree of similarity, and then calculates the third posture information of each of the plurality of different moving bodies.

(15)

The information processing apparatus according to any one of (1) to (14) above, further including:

a communication unit configured to provide the third posture information to another device that performs display control of an object coupled to the movement of the moving body on the basis of the third posture information.

(16)

An information processing method including:

by a computer, acquiring, from an inertial sensor attached to a moving body, inertial information associated with a movement of the moving body;

acquiring first image information obtained by imaging the moving body from a first camera; and calculating third posture information on the basis of first posture information of the moving body obtained on the basis of the inertial information and second posture information of the moving body obtained on the basis of the first image information.

(17)

An information processing program for causing a computer to function as an information processing apparatus including:

a first acquisition unit configured to acquire, from an inertial sensor attached to a moving body, inertial information associated with a movement of the moving body;

a second acquisition unit configured to acquire first image information obtained by imaging the moving body from a first camera; and a calculation unit configured to calculate third posture information on the basis of first posture information of the moving body obtained on the basis of the inertial information acquired by the first acquisition unit and second posture information of the moving body obtained on the basis of the first image information acquired by the second acquisition unit.

REFERENCE SIGNS LIST

10 Sensor device
30 Distribution server
100 Information processing apparatus
110 Operation unit
120 Display unit
130 Communication unit
140 Camera
150 Storage unit
160 Control unit
161 Acquisition unit
162 Inertial data acquisition unit
163 Optical data acquisition unit
166 Calculation unit
168 Display control unit
800 Data use apparatus

The invention claimed is:

1. An information processing method comprising:

receiving, from at least one inertial sensor attached to a moving body, first posture information associated with a movement of the moving body;

receiving second posture information obtained by capturing at least one image of the moving body; and calculating third posture information based on the first posture information of the moving body, and the second posture information of the moving body, wherein the third posture information is calculated using a combination of the first posture information and the second posture information.

2. The information processing method according to claim 1, wherein the moving body includes a human or an animal.

3. The information processing method according to claim 1, wherein the third posture information is calculated by correcting the first posture information based on the second posture information.

4. The information processing method according to claim 1, further comprising:

controlling a display to display an avatar corresponding to the movement of the moving body based on the third posture information.

5. The information processing method according to claim 4, further comprising:

performing, in a case of detecting contact of at least one part of the moving body with a target object based on the at least one image, display control of the avatar in response to the detected contact.

6. The information processing method according to claim 4, further comprising:

detecting expression information of the moving body based on the at least one image; and performing display control of the avatar based on the detected expression information.

7. The information processing method according to claim 4, further comprising:

detecting finger information of the moving body based on the at least one image; and performing display control of the avatar based on the detected finger information.

8. The information processing method according to claim 1, wherein a number of the at least one inertial sensor is six.

9. The information processing method according to claim 8, wherein one inertial sensor is configured to be attached to a waist of the moving body, two inertial sensors are configured to be attached to wrists of the moving body, two inertial sensors are configured to be attached to ankles of the moving body, and one inertial sensor is configured to be attached to a head of the moving body.

10. The information processing method according to claim 1, wherein a number of the at least one inertial sensor is twelve.

11. The information processing method according to claim 1, further comprising:

controlling a display to display an avatar to which the calculated third posture information is applied.

12. The information processing method according to claim 1, further comprising:

controlling a display to display an image of the moving body captured by a camera; and controlling the display to display skeletal information superimposed on the captured image of the moving body.

13. The information processing method according to claim 1, further comprising:

controlling capture of an upright posture of the moving body during a calibration process.

14. The information processing method according to claim 13, wherein the moving body is required to walk at least one step toward to the camera during the calibration process.

15. An information processing system comprising:

circuitry configured to receive, from at least one inertial sensor attached to a moving body, first posture information associated with a movement of the moving body, receive second posture information obtained by capturing at least one image of the moving body, and calculate third posture information based on the first posture information of the moving body, and the second posture information of the moving body, wherein the circuitry calculates the third posture information using a combination of the first posture information and the second posture information.

16. A non-transitory computer-readable storage medium having embodied thereon an information processing program, which when executed by a computer causes the computer to execute a method, the method comprising:

receiving, from at least one inertial sensor attached to a moving body, first posture information associated with a movement of the moving body;

receiving second posture information obtained by capturing at least one image of the moving body; and calculating third posture information based on the first posture information of the moving body, and the second posture information of the moving body, wherein the third posture information is calculated using a combination of the first posture information and the second posture information.

17. The non-transitory computer-readable storage medium according to claim 16, wherein the method further comprises:

controlling a display to display an avatar to which the calculated third posture information is applied.

18. The non-transitory computer-readable storage medium according to claim 16, wherein the method further comprises:

controlling a display to display an image of the moving body captured by a camera; and controlling the display to display skeletal information superimposed on the captured image of the moving body.

19. The non-transitory computer-readable storage medium according to claim 16, wherein the method further comprises:

controlling capture of an upright posture of the moving body during a calibration process.

20. The non-transitory computer-readable storage medium according to claim 16, wherein the moving body is required to walk at least one step toward to the camera during the calibration process.

* * * * *